United States Patent
Lincecum et al.

(10) Patent No.: US 11,014,990 B2
(45) Date of Patent: *May 25, 2021

(54) ANTI-CD40L ANTIBODIES

(71) Applicant: ALS Therapy Development Institute, Cambridge, MA (US)

(72) Inventors: John M. Lincecum, Jamaica Plain, MA (US); Bingbing Jiang, Brighton, MA (US); Steven N. Perrin, Newbury, MA (US); Alan Gill, Reading, MA (US); Cynthia A. Gill, Reading, MA (US); Fernando G. Vieira, Boston, MA (US)

(73) Assignee: ALS Therapy Development Institute, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/931,315

(22) Filed: May 13, 2020

(65) Prior Publication Data

US 2020/0277391 A1 Sep. 3, 2020

Related U.S. Application Data

(60) Division of application No. 16/125,317, filed on Sep. 7, 2018, now Pat. No. 10,683,356, which is a division of application No. 15/667,477, filed on Aug. 2, 2017, now Pat. No. 10,106,618, which is a continuation of application No. PCT/US2016/016165, filed on Feb. 2, 2016.

(60) Provisional application No. 62/111,261, filed on Feb. 3, 2015.

(51) Int. Cl.
A61K 39/395 (2006.01)
C07K 16/28 (2006.01)
A61K 45/06 (2006.01)

(52) U.S. Cl.
CPC ...... *C07K 16/2875* (2013.01); *A61K 39/3955* (2013.01); *A61K 45/06* (2013.01); *C07K 2317/24* (2013.01); *C07K 2317/52* (2013.01); *C07K 2317/71* (2013.01); *C07K 2317/76* (2013.01); *C07K 2317/94* (2013.01)

(58) Field of Classification Search
None
See application file for complete search history.

(56) References Cited

U.S. PATENT DOCUMENTS

| | | |
|---|---|---|
| 5,474,771 A | 12/1995 | Lederman et al. |
| 5,637,481 A | 6/1997 | Ledbetter et al. |
| 5,851,795 A | 12/1998 | Linsley et al. |
| 5,961,974 A | 10/1999 | Armitage et al. |
| 5,962,406 A | 10/1999 | Armitage et al. |
| 6,001,358 A | 12/1999 | Black et al. |
| 6,328,964 B1 | 12/2001 | Noelle et al. |
| 6,340,459 B1 | 1/2002 | Yellin et al. |
| 6,376,459 B1 | 4/2002 | Aruffo et al. |
| 6,451,310 B1 | 9/2002 | Lederman et al. |
| 6,838,261 B1 | 1/2005 | Siegall et al. |
| 7,070,777 B1 | 7/2006 | Lederman et al. |
| 7,173,046 B2 | 2/2007 | Zheng et al. |
| 7,547,438 B2 | 6/2009 | Thomas et al. |
| 7,563,443 B2 | 7/2009 | Grant et al. |
| 7,647,438 B1 | 1/2010 | Norrie et al. |
| 8,293,237 B2 | 10/2012 | Burkly et al. |
| 8,647,625 B2 | 2/2014 | Van Vlijmen et al. |
| 8,784,823 B2 | 7/2014 | Burkly et al. |
| 8,895,010 B2 | 11/2014 | Nadler et al. |
| 8,981,072 B2 | 3/2015 | Nadler et al. |
| 9,028,826 B2 | 5/2015 | Noelle |
| 9,044,459 B2 | 6/2015 | Perrin et al. |
| 9,228,018 B2 | 1/2016 | Nadler et al. |
| 10,106,618 B2 * | 10/2018 | Lincecum ............... A61P 25/28 |
| 10,683,356 B2 * | 6/2020 | Lincecum ............... A61P 29/00 |
| 2001/0018041 A1 | 8/2001 | Hanna et al. |
| 2004/0006208 A1 | 1/2004 | Karpusas et al. |
| 2004/0110226 A1 | 6/2004 | Lazar et al. |
| 2007/0048300 A1 | 3/2007 | Taylor et al. |
| 2007/0190053 A1 | 8/2007 | Kalled et al. |
| 2008/0138349 A1 | 6/2008 | Stavenhagen et al. |
| 2011/0172400 A1 | 7/2011 | Grant et al. |
| 2012/0251531 A1 | 10/2012 | Baehner et al. |
| 2013/0045219 A1 | 2/2013 | Burkly et al. |
| 2013/0095109 A1 | 4/2013 | Nadler et al. |
| 2014/0099317 A1 * | 4/2014 | Suri ....................... A61P 37/02 424/139.1 |
| 2014/0220031 A1 | 8/2014 | Van Vlijmen et al. |
| 2014/0302016 A1 | 10/2014 | Burkly et al. |
| 2015/0104450 A1 | 4/2015 | Minter et al. |
| 2016/0075790 A1 | 3/2016 | Nadler et al. |

FOREIGN PATENT DOCUMENTS

| | | |
|---|---|---|
| EP | 2399936 A2 | 12/2011 |
| JP | 2012511014 A | 5/2012 |
| JP | 2012515556 A | 7/2012 |

(Continued)

OTHER PUBLICATIONS

Abcam, "Anti-GAL4 antibody [5C8]," 2012, 2 pages.
Baker et al., "Identification and Removal of Immunogenicity in Therapeutic Proteins," Current Opinion in Drug Discovery & Development, 2007, vol. 10, No. 2, pp. 219-227.
Bosco et al., "Wild-type and mutant SOD1 share an aberrant Conformation and a common pathogenic pathway in ALS", Nat. Neurosci., 2010, vol. 13, No. 11, pp. 1396-1403.
Chen et al., "Enhacement and Destruction of Antibody Function by Somatic Mutation: Unequal Occurrence is Controlled by V Gene Combinatorial Associations," EMBO J., 2995, vol. 14, pp. 2784-2794.
Colman, P. M. "A Structural View of Immune Recognition by Antobodies," Research in Immunology, 1994, vol. 145, pp. 33-36.

(Continued)

*Primary Examiner* — Phillip Gambel
(74) *Attorney, Agent, or Firm* — Cynthia M. Bott; Honigman LLP

(57) ABSTRACT

Anti-human CD40L antibodies engineered to lack the ability to activate platelets and methods for treating patients having a CD40L-associated disease.

10 Claims, 16 Drawing Sheets

Specification includes a Sequence Listing.

(56) References Cited

FOREIGN PATENT DOCUMENTS

| | | |
|---|---|---|
| JP | 2014530611 A | 11/2014 |
| WO | 1995006481 A1 | 3/1995 |
| WO | 1996040246 A1 | 12/1996 |
| WO | 1998052606 A1 | 11/1998 |
| WO | 1999051258 A1 | 10/1999 |
| WO | 2001083755 A2 | 11/2001 |
| WO | 2002004021 A1 | 1/2002 |
| WO | 2002018445 A2 | 3/2002 |
| WO | 2004037204 A2 | 5/2004 |
| WO | 2005003174 A1 | 1/2005 |
| WO | 2005003175 A1 | 1/2005 |
| WO | 2005011376 A2 | 2/2005 |
| WO | 2006029879 A2 | 3/2006 |
| WO | 2006138316 A2 | 12/2006 |
| WO | 2007059332 A2 | 5/2007 |
| WO | 2007076354 A2 | 7/2007 |
| WO | 2008118356 A2 | 10/2008 |
| WO | 2008143954 A2 | 11/2008 |
| WO | 2010023482 A2 | 3/2010 |
| WO | 2010065819 A1 | 6/2010 |
| WO | 2010085682 A2 | 7/2010 |
| WO | 2012103218 A1 | 8/2012 |
| WO | 2012138768 A2 | 10/2012 |
| WO | 2013056068 A1 | 4/2013 |
| WO | 2013033008 A9 | 6/2013 |
| WO | 2015143209 A1 | 9/2015 |
| WO | 2015164595 A1 | 10/2015 |
| WO | 2016028810 A1 | 2/2016 |

OTHER PUBLICATIONS

D'Angelo et al., "Many Routes to an Antibody Heavy-Chain CDR3: Necessary, Yet Insufficient, for Specific Binding, Frontiers in Immunology," Frontiers in Immunology, Original Research, Mar. 2018, vol. 9, Article 395 doi:10.3389/immu.2018.00395.

Daley et al., "Fc-Disabled Anti-Mouse CD40L Antibodies Retain Efficacy in Promoting Transplantation Tolerance," Am J Transplantation, 2008, vol. 8, pp. 2265-2271.

Davis et al., "Abatacept binds to the Fc receptor CD64 but does not mediate complement-dependent cytotoxicity or antibody-dependent cellular cytotoxicity," J. Rheumatol., 2007, vol. 34, No. 11, pp. 2204-2210.

Dumont et al., "IDEC-131. IDEC/Eisai," Curr Opin Invenstig Drugs, 2002, pp. 725-734, vol. 3, No. 5.

Extended European Search Report for EP16747111, dated Jul. 4, 2018, 11 pages.

Gilliland "Rapid and Reliable Cloning of Antibody Variable Regions and Generation of Recombinant Single Chain Antibody Fragments", Tissue Antigens, 1996, vol. 47, pp. 1-20.

Gruzman et al., "Common Molecular Signature in SOD1 for both Sporadic and Familial Amyotrophic Lateral Sclerosis", PNAS, 2007, vol. 104, No. 30, pp. 12524-12529.

Holgate et al., "Circumventing Immunogenicity in the Development of Therapeutic Antibodies," Idrugs, 2009, vol. 12, No. 4, pp. 233-237.

Imgenex, Monoclonal Antibody to IGF-1R (Clone 24-31), accessed Sep. 21, 2012, 2 pgs.

International Search Report and Written Opinion for PCT Application No. PCT/US2016/016165, dated Jul. 5, 2016, 11 pages.

International Search Report and Written Opinion for PCT/Neuro—US2009/066715, dated Mar. 22, 2010, 11 pages.

Kallmeier et al., "Poster—Improvements to the GS System for Easier Re-expression of Human Antibodies," 1 page.

Karpusas et al., "Structure of CD40 Ligand in Complex with the Fab Fragment of a Neutralizing Humanized Antibody," Structure, 2001, vol. 9, No. 4, pp. 321-329.

Ke et al, "CD40-CD40L interactions promote neuronal death in a model of neurodegeneration due to mild impairment of oxidative metabolism", Neurochemistry International, 2005, pp. 204-215, vol. 47, No. 3.

Kiaei et al, "Celastrol blocks neuronal cell death and extends life in transgenic mouse model of amyotrophic lateral sclerosis," Neurodegenerative Diseases, 2005, pp. 246-254, vol. 2, No. 5.

Kirk et al., "CTLA4-Ig and anti-CD40 Ligand Prevent Renal Allograft Rejection in Primates", Proc Natl Acad Sci USA, 1997, vol. 94, pp. 8789-8794.

Knosalla et al., "Intial Experience with the Humna Anti-human CD154 Monoclonal Antibody, ABI793, in Pig-to-baboon Xenotransplantation", Xenotransplantation, 2004, vol. 11, pp. 353-360.

Kussie et al., "a Single Engineered Amino Acid Subsitution Changes Antibody Fine Specificity," 1994, J. Immunol., vol. 152, pp. 146-152.

Law et al., "Preclinical Antilymphoma Activity of a Human Anti-CD40 Monoclonal Antibody, SGN-40", Cancer Res, 2005, vol. 65, No. 18, pp. 8331-88338.

Lederman et al., Identification of a Novel Surface Protein on Activated CD4+ T Cells that Induces Contact-dependent B Cell Differentiation (Help), J Exp Med, 1992, vol. 175, pp. 1091-1101.

Leitner et al., Working with ALS Mice:, The Jackson Laboratory, Oct. 14, 2009.

Lincecum, J. M., et al., "From Transcriptome Analysis to Therapeutic anti-CD40L Treatement in the SOD1 Model of Amyotrophic Lateral Sclerosis", Nature Genetics, 2010, pp. 1-10.

Linsley et al., "CTLA-4 is a Second Receptor for the B Cell Activation Antigen B7," J. Exp. Med., 1991, vol. 174, No. 3, pp. 561-569.

Ludolph et al., "Guidelines for Preclinical Animal Research in ALS/MND: A Consensus Meeting," Amyotrophic Lateral Sclerosis, 2010, vol. 11, pp. 38-45.

Madsen A., Building a Better Mouse: How Animal Models Help Fight ALS, MDA/ALS Newsmagazine, Sep. 1, 2010, vol. 15, No. 5, 4 pages.

National Institute of Neurological Disorders and Stroke (NINDS), "Amyotrophic Lateral Sclerosis (ALS) Fact Sheet", NIH Internet Publication relating to ALS accessed Nov. 19, 2012.

Okuno et al., "Induction of cyclooxygenase-2 in reactive glial cells by the CD40 pathway: relevance to amyotrophic lateral sclerosis," Journal of Neurochemistry, 2004, vol. 91, No. 2, pp. 404-412.

Piche-Nicholas et al., "Changes in complemetarity-determining regions significantly alter IgG binding to the neonatal Fc receptor (FcRN) and pharmacokinetics," MABS, 2018, vol. 10, No. 1, pp. 81-94, oi.org/10.1080/19420862.2017.1389355.

Rudikoff et al., "Single Amino Acid Substitution Altering Antigen-binding Specificity," Proc Natl Acad Sci USA, Mar. 1982, vol. 79, pp. 1979-1983.

Santa Cruz Biotechnology Inc., accessed Sep. 21, 2012, 1 pg.

"Seattle Genetics Receives Key U.S. Patents for SGN-40 Program," Jan. 19, 2005, http://www.seattlegenetics.com/, Posted by MMSupport.net, http://www.mmsupport.net/seattle-genetics-receives-key-Neuro - US-patents-for-sgn-40-program/, 3 pages.

Starzl et al., "Refinements in the Surgical Technique of Liver Transplantation," Semin Liver Dis., 1985, vol. 5, No. 4, pp. 349-356.

Tai et al., "Mechanisms by Which SGN-40, a Humanized Anti-CD40 Antibody, Induces Cytotoxicity in Human Multiple Myeloma Cells: Clinical Implications", Cancer Rersearch, 2004, vol. 64, pp. 2846-2852.

Traynor et al., "Neuroprotective agents for clinical trials in ALS: A systematic assessment," Neurology, 2006, vol. 67, pp. 20-27.

Vainzof et al., "Animal Models for Genetic Neuromuscular Diseases," J. Mol. Neurosci., 2008, pp. 241-248, vol. 34.

Van Blitterswijk et al., "Anti-superoxide Dismutase Antibodies are Associated with Survival in Patients with Sporadic Amyotrophic Lateral Sclerosis", Amyotroph Lateral Scler, 2011, vol. 12, No. 6, pp. 430-438.

Viglietta et al., "CTLA4lg Treatment in Patients With Multiple Sclerosis", Neurology, 2008, vol. 71, No. 12, pp. 917-924.

Xie et al., "Engineering of a Novel Anti-CD40L Domain Antibody for Treatment of Autoimmune Diseases," J. Immunol., 2014, vol. vol. 192, No. 9, pp. 4083-4092.

\* cited by examiner

FIG. 1A

Heavy chain hu5c8 (SEQ ID NO: 21)

```
QVQLVQSGAE VVKPGASVKL SCKASGYIFT SYYMYWVKQA PGQGLEWIGE
INPSNGDTNF NEKFKSKATL TVDKSASTAY MELSSLRSED TAVYYCTRSD
GRNDMDSWGQ GTLVTVSSAS TKGPSVFPLA PSSKSTSGGT AALGCLVKDY
FPEPVTVSWN SGALTSGVHT FPAVLQSSGL YSLSSVVTVP SSSLGTQTYI
CNVNHKPSNT KVDKKVEPKS CDKTHTCPPC PAPELLGGPS VFLFPPKPKD
TLMISRTPEV TCVVVDVSHE DPEVKFNWYV DGVEVHNAKT KPREEQYNST
YRVVSVLTVL HQDWLNGKEY KCKVSNKALP APIEKTISKA KGQPREPQVY
TLPPSRDELT KNQVSLTCLV KGFYPSDIAV EWESNGQPEN NYKTTPPVLD
SDGSFFLYSK LTVDKSRWQQ GNVFSCSVMH EALHNHYTQK SLSLSPGK
```

FIG. 1B

Heavy chain JB5 (SEQ ID NO: 9)

```
QVQLVQSGAE VVKPGASVKL SCKASGYIFT SYYMYWVKQA PGQGLEWIGE
INPSNGDTNF NEKFKSKATL TVDKSASTAY MELSSLRSED TAVYYCTRSD
GRNDMDSWGQ GTLVTVSSAS TKGPSVFPLA PSSKSTSGGT AALGCLVKDY
FPEPVTVSWN SGALTSGVHT FPAVLQSSGL YSLSSVVTVP SSSLGTQTYI
CNVNHKPSNT KVDKKVEPKS SDKTHTSPPS PAPELLGGSS VFLFPPKPKD
TLMISRTPEV TCVVVDVSHE DPEVKFNWYV DGVEVHNAKT KPREEQYNST
YRVVSVLTVL HQDWLNGKEY KCKVSNKALP APIEKTISKA KGQPREPQVY
TLPPSRDELT KNQVSLTCLV KGFYPSDIAV EWESNGQPEN NYKTTPPVLD
SDGSFFLYSK LTVDKSRWQQ GNVFSCSVMH EALHNHYTQK SLSLSPGK
```

FIG. 1C

Heavy chain JB5-K74R (SEQ ID NO: 13)

```
QVQLVQSGAE VVKPGASVKL SCKASGYIFT SYYMYWVKQA PGQGLEWIGE
INPSNGDTNF NEKFKSKATL TVDRSASTAY MELSSLRSED TAVYYCTRSD
GRNDMDSWGQ GTLVTVSSAS TKGPSVFPLA PSSKSTSGGT AALGCLVKDY
FPEPVTVSWN SGALTSGVHT FPAVLQSSGL YSLSSVVTVP SSSLGTQTYI
CNVNHKPSNT KVDKKVEPKS SDKTHTSPPS PAPELLGGSS VFLFPPKPKD
TLMISRTPEV TCVVVDVSHE DPEVKFNWYV DGVEVHNAKT KPREEQYNST
YRVVSVLTVL HQDWLNGKEY KCKVSNKALP APIEKTISKA KGQPREPQVY
TLPPSRDELT KNQVSLTCLV KGFYPSDIAV EWESNGQPEN NYKTTPPVLD
SDGSFFLYSK LTVDKSRWQQ GNVFSCSVMH EALHNHYTQK SLSLSPGK
```

FIG. 2A

Light Chain JB5 (SEQ ID NO: 7)

```
DIVLTQSPAT LSVSPGERAT ISCRASQRVS SSTYSYMHWY QQKPGQPPKL
LIKYASNLES GVPARFSGSG SGTDFTLTIS SVEPEDFATY YCQHSWEIPP
TFGGGTKLEI KRTVAAPSVF IFPPSDEQLK SGTASVVCLL NNFYPREAKV
QWKVDNALQS GNSQESVTEQ DSKDSTYSLS STLTLSKADY EKHKVYACEV
THQGLSSPVT KSFNRGEC
```

FIG. 2B

Light Chain JB5-R28K (SEQ ID NO: 11)

```
DIVLTQSPAT LSVSPGEKAT ISCRASQKVS SSTYSYMHWY QQKPGQPPKL
LIKYASNLES GVPARFSGSG SGTDFTLTIS SVEPEDFATY YCQHSWEIPP
TFGGGTKLEI KRTVAAPSVF IFPPSDEQLK SGTASVVCLL NNFYPREAKV
QWKVDNALQS GNSQESVTEQ DSKDSTYSLS STLTLSKADY EKHKVYACEV
THQGLSSPVT KSFNRGEC
```

FIG. 2C

Fc region of hu5c8 (SEQ ID NO: 3)

```
EPKSCDKTHT CPPCPAPELL GGPSVFLFPP KPKDTLMISR TPEVTCVVVD
VSHEDPEVKF NWYVDGVEVH NAKTKPREEQ YNSTYRVVSV LTVLHQDWLN
GKEYKCKVSN KALPAPIEKT ISKAKGQPRE PQVYTLPPSR DELTKNQVSL
TCLVKGFYPS DIAVEWESNG QPENNYKTTP PVLDSDGSFF LYSKLTVDKS
RWQQGNVFSC SVMHEALHNH YTQKSLSLSP GK
```

FIG. 2D

Fc region of JB5 (SEQ ID NO: 4)

```
EPKSSDKTHT SPPSPAPELL GGSSVFLFPP KPKDTLMISR TPEVTCVVVD
VSHEDPEVKF NWYVDGVEVH NAKTKPREEQ YNSTYRVVSV LTVLHQDWLN
GKEYKCKVSN KALPAPIEKT ISKAKGQPRE PQVYTLPPSR DELTKNQVSL
TCLVKGFYPS DIAVEWESNG QPENNYKTTP PVLDSDGSFF LYSKLTVDKS
RWQQGNVFSC SVMHEALHNH YTQKSLSLSP GK
```

FIG. 15

| SEQ ID NO: | Description | Sequence |
|---|---|---|
| 1 | hu5c8 and JB5 VL region | DIVLTQSPATLSVSPGERATISCRASQRVSSSTYSYMHWYQQKPGQPPKLLIKYASNLESGVPARFSGSGSGTDFTLTISSVEPEDFATYYCQHSWEIPPTFGGGTKLEIK |
| 2 | hu5c8 and JB5 VH region | QVQLVQSGAEVVKPGASVKLSCKASGYIFTSYYMYWVKQAPGQGLEWIGEINPSNGDTNFNEKFKSKATLTVDKSASTAYMELSSLRSEDTAVYYCTRSDGRNDMDSWGQGTLVTVSS |
| 3 | Fc region | EPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 4 | JB5 Fc region | EPKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 5 | JB5-R28K VL region | DIVLTQSPATLSVSPGERATISCRASQKVSSSTYSYMHWYQQKPGQPPKLLIKYASNLESGVPARFSGSGSGTDFTLTISSVEPEDFATYYCQHSWEIPPTFGGGTKLEIK |
| 6 | JB5-K74R VH region | QVQLVQSGAEVVKPGASVKLSCKASGYIFTSYYMYWVKQAPGQGLEWIGEINPSNGDTNFNEKFKSKATLTVDRSASTAYMELSSLRSEDTAVYYCTRSDGRNDMDSWGQGTLVTVSS |
| 7 | JB5 light chain Amino acid sequence | DIVLTQSPATLSVSPGERATISCRASQRVSSSTYSYMHWYQQKPGQPPKLLIKYASNLESGVPARFSGSGSGTDFTLTISSVEPEDFATYYCQHSWEIPPTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

FIG. 16

| SEQ ID NO: | Description | Sequence |
|---|---|---|
| 8 | JB light chain nucleotide sequence | GACATCGTGCTGACCCAGTCCCCCGCCACCCTGTCCGTGTCCCCCGGCGA GAGGGCCACCATCTCCTGCAGGGCCTCCCAGAGGGTGTCCTCCTCCACCT ACTCCTACATGCACTGGTACCAGCAGAAGCCCGGCCAGCCCCCCAAGCTG CTGATCAAGTACGCCTCCAACCTGGAGTCCGGCGTGCCCGCCAGGTTCTC CGGCTCCGGCTCCGGCACCGACTTCACCCTGACCATCTCCTCCGTGGAGC CCGAGGACTTCGCCACCTACTACTGCCAGCACTCCTGGGAGATCCCCCCC ACCTTCGGCGGCGGCACCAAGCTGgaaatcaaaCGTACGGTGGCTGCACC ATCTGTCTTCATCTTCCCGCCATCTGATGAGCAGTTGAAATCTGGAACTG CCTCTGTTGTGTGCCTGCTGAATAACTTCTATCCCAGAGAGGCCAAAGTA CAGTGGAAGGTGGATAACGCCCTCCAATCGGGTAACTCCCAGGAGAGTGT CACAGAGCAGGACAGCAAGGACAGCACCTACAGCCTCAGCAGCACCCTGA CGCTGAGCAAAGCAGACTACGAGAAACACAAAGTCTACGCCTGCGAAGTC ACCCATCAGGGCCTGAGCTCGCCCGTCACAAAGAGCTTCAACAGGGGAGA GTGTTAGTGA |
| 9 | JB5 heavy chain amino acid sequence | QVQLVQSGAEVVKPGASVKLSCKASGYIFTSYYMYWVKQAPGQGLEWIGE INPSNGDTNFNEKFKSKATLTVDKSASTAYMELSSLRSEDTAVYYCTRSD GRNDMDSWGQGTLVTVSSASTKGPSVFPLAPSSKSTSGGTAALGCLVKDY FPEPVTVSWNSGALTSGVHTFPAVLQSSGLYSLSSVVTVPSSSLGTQTYI CNVNHKPSNTKVDKKVEPKSSDKTHTSPPSPAPELLGGSSVFLFPPKPKD TLMISRTPEVTCVVVDVSHEDPEVKFNWYVDGVEVHNAKTKPREEQYNST YRVVSVLTVLHQDWLNGKEYKCKVSNKALPAPIEKTISKAKGQPREPQVY TLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK |

FIG. 17

| SEQ ID NO: | Description | Sequence |
|---|---|---|
| 10 | JB5 heavy chain nucleic acid sequence | CAGGTGCAGCTGGTGCAGTCCGGCGCCGAGGTGGTGAAGCCCGGCGCCTC
CGTGAAGCTGTCCTGCAAGGCCTCCGGCTACATCTTCACCTCCTACTACA
TGTACTGGGTGAAGCAGGCCCCCGGCCAGGGCCTGGAGTGGATCGGCGAG
ATCAACCCCTCCAACGGCGACACCAACTTCAACGAGAAGTTCAAGTCCAA
GGCCACCCTGACCGTGGACAAGTCCGCCTCCACCGCCTACATGGAGCTGT
CCTCCCTGAGGTCCGAGGACACCGCCGTGTACTACTGCACCAGGTCCGAC
GGCAGGAACGACATGGACTCCTGGGGCCAGGGCACCCTGGTGACCGTGTC
CTCCGCTAGCACCAAGGGCCCATCGGTCTTCCCCCTGGCACCCTCCTCCA
AGAGCACCTCTGGGGGCACAGCAGCCCTGGGCTGCCTGGTCAAGGACTAC
TTCCCCGAACCGGTGACGGTGTCGTGGAACTCAGGCGCCCTGACCAGCGG
CGTGCACACCTTCCCGGCTGTCCTACAGTCCTCAGGACTCTACTCCCTCA
GCAGCGTGGTGACCGTGCCCTCCAGCAGCTTGGGCACCCAGACCTACATC
TGCAACGTGAATCACAAGCCCAGCAACACCAAGGTGGACAAGAAAGTTGg
tgagaggccagcacagggagggagggtgtctgctggaagccaggctcagc
gctcctgcctggacgcatccggctatgcagcccagtccagggcagcaa
ggcaggccccgtctgcctcttcacccggaggcctctgccgccccactca
tgctcagggagagggtcttctggcttttccccaggctctgggcaggcac
aggctaggtgcccctaacccaggccctgcacacaaaggggcaggtgctgg
gctcagacctgccaagagccatatccgggaggaccctgcccctgacctaa
gccacccaaaggccaaactctccactccctcagctcggacaccttctc
tcctcccagattccagtaactcccaatctctctctgcagAGCCCAAATC
TAGTGACAAAACTCACACAAGCCCACCGAGCCCAGgtaagccagcccagg
cctcgccctccagctcaaggcgggacaggtgccctagagtagcctgcatc
cagggacaggccccagccgggtgctgacacgtccacctccatctcttcct
cagCACCTGAACTCCTGGGGGGATCCTCAGTCTTCCTCTTCCCCCCAAAA
CCCAAGGACACCCTCATGATCTCCCGGACCCCTGAGGTCACATGCGTGGT
GGTGGACGTGAGCCACGAAGACCCTGAGGTCAAGTTCAACTGGTACGTGG
ACGGCGTGGAGGTGCATAATGCCAAGACAAAGCCGCGGGAGGAGCAGTAC
AACAGCACGTACCGTGTGGTCAGCGTCCTCACCGTCCTGCACCAGGACTG
GCTGAATGGCAAGGAGTACAAGTGCAAGGTCTCCAACAAAGCCCTCCCAG
CCCCCATCGAGAAAACCATCTCCAAAGCCAAAGgtgggaccgtggggtg
cgagggccacatggacagaggccggctcggcccaccctctgccctgagag
tgaccgctgtaccaacctctgtccctacagGGCAGCCCCGAGAACCACAG
GTGTACACCCTGCCCCCATCCCGGGATGAGCTGACCAAGAACCAGGTCAG
CCTGACCTGCCTGGTCAAAGGCTTCTATCCCAGCGACATCGCCGTGGAGT
GGGAGAGCAATGGGCAGCCGGAGAACAACTACAAGACCACGCCTCCCGTG
CTGGACTCCGACGGCTCCTTCTTCCTCTACAGCAAGCTCACCGTGGACAA
GAGCAGGTGGCAGCAGGGGAACGTCTTCTCATGCTCCGTGATGCATGAGG
CTCTGCACAACCACTACACACAGAAGAGCCTCTCCCTGTCTCCGGGTAAA
taatga |

FIG. 18

| SEQ ID NO: | Description | Sequence |
|---|---|---|
| 11 | JB5-R28K light chain amino acid sequence | DIVLTQSPATLSVSPGERATISCRASQKVSSSTYSYMHWYQQKPGQPPKL LIKYASNLESGVPARFSGSGSGTDFTLTISSVEPEDFATYYCQHSWEIPP TFGGGTKLEIKRTVAAPSVFIFPPSDEQLKSGTASVVCLLNNFYPREAKV QWKVDNALQSGNSQESVTEQDSKDSTYSLSSTLTLSKADYEKHKVYACEV THQGLSSPVTKSFNRGEC |
| 12 | JB5-R28K light chain nucleic acid sequence | GACATCGTGCTGACCCAGTCCCCCGCCACCCTGTCCGTGTCCCCCGGCGA GAGGGCCACCATCTCCTGCAGGGCCTCCCAGAAGGTGTCCTCCTCCACCT ACTCCTACATGCACTGGTACCAGCAGAAGCCCGGCCAGCCCCCCAAGCTG CTGATCAAGTACGCCTCCAACCTGGAGTCCGGCGTGCCCGCCAGGTTCTC CGGCTCCGGCTCCGGCACCGACTTCACCCTGACCATCTCCTCCGTGGAGC CCGAGGACTTCGCCACCTACTACTGCCAGCACTCCTGGGAGATCCCCCCC ACCTTCGGCGGCGGCACCAAGCTGgaaatcaaaCGTACGGTGGCTGCACC ATCTGTCTTCATCTTCCCGCCATCTGATGAGCAGTTGAAATCTGGAACTG CCTCTGTTGTGTGCCTGCTGAATAACTTCTATCCCAGAGAGGCCAAAGTA CAGTGGAAGGTGGATAACGCCCTCCAATCGGGTAACTCCCAGGAGAGTGT CACAGAGCAGGACAGCAAGGACAGCACCTACAGCCTCAGCAGCACCCTGA CGCTGAGCAAAGCAGACTACGAGAAACACAAAGTCTACGCCTGCGAAGTC ACCCATCAGGGCCTGAGCTCGCCCGTCACAAAGAGCTTCAACAGGGGAGA GTGTTAGTGA |
| 13 | JB5-K74R heavy chain amino acid | QVQLVQSGAEVVKPGASVKLSCKASGYIFTSYYMYWVKQAPGQGLEWIGE INPSNGDTNFNEKFKSKATLTVDRSASTAYMELSSLRSEDTAVYYCTRSD GRNDMDSWGQGTLVTVSSASTKGPSVFPLAPSSKSTSGGTAALGCLVKDY FPEPVTVSWNSGALTSGVHTFPAVLQSSGLYSLSSVVTVPSSSLGTQTYI CNVNHKPSNTKVDKKVEPKSSDKTHTSPPSPAPELLGGSSVFLFPPKPKD TLMISRTPEVTCVVVDVSHEDPEVKFNWYVDGVEVHNAKTKPREEQYNST YRVVSVLTVLHQDWLNGKEYKCKVSNKALPAPIEKTISKAKGQPREPQVY TLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK |

FIG. 19

| SEQ ID NO: | Description | Sequence |
|---|---|---|
| 14 | JB5-K74R heavy chain nucleic acid sequence | CAGGTGCAGCTGGTGCAGTCCGGCGCCGAGGTGGTGAAGCCCGGCGCCTC CGTGAAGCTGTCCTGCAAGGCCTCCGGCTACATCTTCACCTCCTACTACA TGTACTGGGTGAAGCAGGCCCCCGGCCAGGGCCTGGAGTGGATCGGCGAG ATCAACCCCTCCAACGGCGACACCAACTTCAACGAGAAGTTCAAGTCCAA GGCCACCCTGACCGTGGACAGGTCCGCCTCCACCGCCTACATGGAGCTGT CCTCCCTGAGGTCCGAGGACACCGCCGTGTACTACTGCACCAGGTCCGAC GGCAGGAACGACATGGACTCCTGGGGCCAGGGCACCCTGGTGACCGTGTC CTCCGCTAGCACCAAGGGCCCATCGGTCTTCCCCCTGGCACCCTCCTCCA AGAGCACCTCTGGGGGCACAGCAGCCCTGGGCTGCCTGGTCAAGGACTAC TTCCCCGAACCGGTGACGGTGTCGTGGAACTCAGGCGCCCTGACCAGCGG CGTGCACACCTTCCCGGCTGTCCTACAGTCCTCAGGACTCTACTCCCTCA GCAGCGTGGTGACCGTGCCCTCCAGCAGCTTGGGCACCCAGACCTACATC TGCAACGTGAATCACAAGCCCAGCAACACCAAGGTGGACAAGAAAGTTGg tgagaggccagcacagggagggagggtgtctgctggaagccaggctcagc gctcctgcctggacgcatccggctatgcagcccagtccagggcagcaa ggcaggccccgtctgcctcttcacccggaggcctctgccgcccactca tgctcagggagagggtcttctggcttttcccaggctctgggcaggcac aggctaggtgcccctaacccaggccctgcacacaaaggggcaggtgctgg gctcagacctgccaagagccatatccgggaggaccctgcccctgacctaa gccacccaaaggccaaactctccactccctcagctcggacaccttctc tcctcccagattccagtaactcccaatcttctctctgcagAGCCCAAATC TAGTGACAAAACTCACACAAGCCCACCGAGCCCAGgtaagccagcccagg cctcgccctccagctcaaggcgggacaggtgccctagagtagcctgcatc cagggacaggccccagccgggtgctgacacgtccacctccatctcttcct cagCACCTGAACTCCTGGGGGGATCCTCAGTCTTCCTCTTCCCCCCAAAA CCCAAGGACACCCTCATGATCTCCCGGACCCCTGAGGTCACATGCGTGGT GGTGGACGTGAGCCACGAAGACCCTGAGGTCAAGTTCAACTGGTACGTGG ACGGCGTGGAGGTGCATAATGCCAAGACAAAGCCGCGGGAGGAGCAGTAC AACAGCACGTACCGTGTGGTCAGCGTCCTCACCGTCCTGCACCAGGACTG GCTGAATGGCAAGGAGTACAAGTGCAAGGTCTCCAACAAAGCCCTCCCAG CCCCCATCGAGAAAACCATCTCCAAAGCCAAAGgtgggaccgtggggtg cgagggccacatggacagaggccggctcggcccaccctctgccctgagag tgaccgctgtaccaacctctgtccctacagGGCAGCCCCGAGAACCACAG GTGTACACCCTGCCCCCATCCCGGGATGAGCTGACCAAGAACCAGGTCAG CCTGACCTGCCTGGTCAAAGGCTTCTATCCCAGCGACATCGCCGTGGAGT GGGAGAGCAATGGGCAGCCGGAGAACAACTACAAGACCACGCCTCCCGTG CTGGACTCCGACGGCTCCTTCTTCCTCTACAGCAAGCTCACCGTGGACAA GAGCAGGTGGCAGCAGGGGAACGTCTTCTCATGCTCCGTGATGCATGAGG CTCTGCACAACCACTACACACAGAAGAGCCTCTCCCTGTCTCCGGGTAAA taatga |

FIG. 20

| SEQ ID NO: | Description | Sequence |
|---|---|---|
| 15 | JB5 CDR-L1 | ISCRASQRVSSSTYSYMH |
| 16 | JB5 CDR-L2 | YASNLES |
| 17 | JB5 CDR-L3 | QHSWEIPPT |
| 18 | JB5 CDR-H1 | SYYMY |
| 19 | JB5 CDR-H2 | EINPSNGDTNFNEKFKS |
| 20 | JB5 CDR-H3 | SDGRNDMDS |
| 21 | Hu5c8 Heavy Chain | QVQLVQSGAEVVKPGASVKLSCKASGYIFTSYYMYWVKQAPGQGLEWIG EINPSNGDTNFNEKFKSKATLTVDKSASTAYMELSSLRSEDTAVYYCTR SDGRNDMDSWGQGTLVTVSSASTKGPSVFPLAPSSKSTSGGTAALGCLV KDYFPEPVTVSWNSGALTSGVHTFPAVLQSSGLYSLSSVVTVPSSSLGT QTYICNVNHKPSNTKVDKKVEPKSCDKTHTCPPCPAPELLGGPSVFLFP PKPKDTLMISRTPEVTCVVVDVSHEDPEVKFNWYVDGVEVHNAKTKPRE EQYNSTYRVVSVLTVLHQDWLNGKEYKCKVSNKALPAPIEKTISKAKGQ PREPQVYTLPPSRDELTKNQVSLTCLVKGFYPSDIAVEWESNGQPENNY KTTPPVLDSDGSFFLYSKLTVDKSRWQQGNVFSCSVMHEALHNHYTQKS LSLSPGK |

SEQUENCE LISTING

```
<160> NUMBER OF SEQ ID NOS: 25

<210> SEQ ID NO 1
<211> LENGTH: 111
<212> TYPE: PRT
<213> ORGANISM: Artificial Sequence
<220> FEATURE:
<223> OTHER INFORMATION: Synthetically Generated Sequence

<400> SEQUENCE: 1

Asp Ile Val Leu Thr Gln Ser Pro Ala Thr Leu Ser Val Ser Pro Gly
1               5                   10                  15

Glu Arg Ala Thr Ile Ser Cys Arg Ala Ser Gln Arg Val Ser Ser Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Gln His Ser Trp
                85                  90                  95

Glu Ile Pro Pro Thr Phe Gly Gly Gly Thr Lys Leu Glu Ile Lys
            100                 105                 110

<210> SEQ ID NO 2
<211> LENGTH: 118
<212> TYPE: PRT
<213> ORGANISM: Artificial Sequence
<220> FEATURE:
<223> OTHER INFORMATION: Synthetically Generated Sequence

<400> SEQUENCE: 2

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser
        115

<210> SEQ ID NO 3
<211> LENGTH: 232
<212> TYPE: PRT
```

<213> ORGANISM: Artificial Sequence
<220> FEATURE:
<223> OTHER INFORMATION: Synthetically Generated Sequence

<400> SEQUENCE: 3

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 4
<211> LENGTH: 232
<212> TYPE: PRT
<213> ORGANISM: Artificial Sequence
<220> FEATURE:
<223> OTHER INFORMATION: Synthetically Generated Sequence

<400> SEQUENCE: 4

Glu Pro Lys Ser Ser Asp Lys Thr His Thr Ser Pro Pro Ser Pro Ala
1               5                   10                  15

Pro Glu Leu Leu Gly Gly Ser Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

```
Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 5
<211> LENGTH: 111
<212> TYPE: PRT
<213> ORGANISM: Artificial Sequence
<220> FEATURE:
<223> OTHER INFORMATION: Synthetically Generated Sequence

<400> SEQUENCE: 5

Asp Ile Val Leu Thr Gln Ser Pro Ala Thr Leu Ser Val Ser Pro Gly
1               5                   10                  15

Glu Arg Ala Thr Ile Ser Cys Arg Ala Ser Gln Lys Val Ser Ser Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Gln His Ser Trp
                85                  90                  95

Glu Ile Pro Pro Thr Phe Gly Gly Gly Thr Lys Leu Glu Ile Lys
            100                 105                 110

<210> SEQ ID NO 6
<211> LENGTH: 118
<212> TYPE: PRT
<213> ORGANISM: Artificial Sequence
<220> FEATURE:
<223> OTHER INFORMATION: Synthetically Generated Sequence

<400> SEQUENCE: 6

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60
```

Lys Ser Lys Ala Thr Leu Thr Val Asp Arg Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser
        115

<210> SEQ ID NO 7
<211> LENGTH: 218
<212> TYPE: PRT
<213> ORGANISM: Artificial Sequence
<220> FEATURE:
<223> OTHER INFORMATION: Synthetically Generated Sequence

<400> SEQUENCE: 7

Asp Ile Val Leu Thr Gln Ser Pro Ala Thr Leu Ser Val Ser Pro Gly
1               5                   10                  15

Glu Arg Ala Thr Ile Ser Cys Arg Ala Ser Gln Arg Val Ser Ser Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Gln His Ser Trp
                85                  90                  95

Glu Ile Pro Pro Thr Phe Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 8
<211> LENGTH: 660
<212> TYPE: DNA
<213> ORGANISM: Artificial Sequence
<220> FEATURE:
<223> OTHER INFORMATION: Synthetically Generated Sequence

<400> SEQUENCE: 8
gacatcgtgc tgacccagtc ccccgccacc ctgtccgtgt cccccggcga gagggccacc    60
atctcctgca gggcctccca gagggtgtcc tcctccacct actcctacat gcactggtac   120

```
cagcagaagc cggccagcc ccccaagctg ctgatcaagt acgcctccaa cctggagtcc    180
ggcgtgcccg ccaggttctc cggctccggc tccggcaccg acttcaccct gaccatctcc    240
tccgtggagc ccgaggactt cgccacctac tactgccagc actcctggga gatccccccc    300
accttcggcg gcggcaccaa gctggaaatc aaacgtacgg tggctgcacc atctgtcttc    360
atcttcccgc catctgatga gcagttgaaa tctggaactg cctctgttgt gtgcctgctg    420
aataacttct atcccagaga ggccaaagta cagtggaagg tggataacgc cctccaatcg    480
ggtaactccc aggagagtgt cacagagcag gacagcaagg acagcaccta cagcctcagc    540
agcaccctga cgctgagcaa agcagactac gagaaacaca agtctacgc ctgcgaagtc    600 acccatcagg gcctgagctc gcccgtcaca aagagcttca caggggaga gtgttagtga    660
```

<210> SEQ ID NO 9
<211> LENGTH: 448
<212> TYPE: PRT
<213> ORGANISM: Artificial Sequence
<220> FEATURE:
<223> OTHER INFORMATION: Synthetically Generated Sequence

<400> SEQUENCE: 9

```
Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Ser Asp Lys Thr
    210                 215                 220

His Thr Ser Pro Pro Ser Pro Ala Pro Glu Leu Leu Gly Gly Ser Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270
```

Glu Val Lys Phe Asn Trp Tyr Val Asp Gly Val Glu Val His Asn Ala
             275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 10
<211> LENGTH: 1956
<212> TYPE: DNA
<213> ORGANISM: Artificial Sequence
<220> FEATURE:
<223> OTHER INFORMATION: Synthetically Generated Sequence

<400> SEQUENCE: 10
caggtgcagc tggtgcagtc cggcgccgag gtggtgaagc ccggcgcctc cgtgaagctg      60
tcctgcaagg cctccggcta catcttcacc tcctactaca tgtactgggt gaagcaggcc     120
cccggccagg gcctggagtg gatcggcgag atcaaccccc tcaacggcga caccaacttc     180
aacgagaagt tcaagtccaa ggccaccctg accgtggaca gtccgcctc accgcctac      240 atggagctgt cctccctgag gtccgaggac accgccgtgt actactgcac caggtccgac     300
ggcaggaacg acatggactc ctggggccag ggcaccctgg tgaccgtgtc ctccgctagc     360
accaagggcc catcggtctt ccccctggca ccctcctcca agagcacctc tgggggcaca     420
gcagccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct gggcacccca gacctacatc     600
tgcaacgtga atcacaagcc cagcaacacc aaggtggaca agaaagttgg tgagaggcca     660
gcacagggag ggagggtgtc tgctggaagc caggctcagc gctcctgcct ggacgcatcc     720
cggctatgca gccccagtcc agggcagcaa ggcaggcccc gtctgcctct tcacccggag     780
gcctctgccc gccccactca tgctcaggga gaggtcttc tggcttttc cccaggctct     840 gggcaggcac aggctaggtg ccctaaccc aggccctgca cacaagggg caggtgctgg      900 gctcagacct gccaagagcc atatccggga ggaccctgcc cctgacctaa gcccacccca     960
aaggccaaac tctccactcc ctcagctcgg acaccttctc tcctcccaga ttccagtaac    1020
tcccaatctt ctctctgcag agcccaaatc tagtgacaaa actcacacaa gcccaccgag    1080

```
cccaggtaag ccagcccagg cctcgccctc cagctcaagg cgggacaggt gccctagagt    1140
agcctgcatc cagggacagg ccccagccgg gtgctgacac gtccacctcc atctcttcct    1200
cagcacctga actcctgggg ggatcctcag tcttcctctt ccccccaaaa cccaaggaca    1260
ccctcatgat ctcccggacc cctgaggtca catgcgtggt ggtggacgtg agccacgaag    1320
accctgaggt caagttcaac tggtacgtgg acggcgtgga ggtgcataat gccaagacaa    1380
agccgcggga ggagcagtac aacagcacgt accgtgtggt cagcgtcctc accgtcctgc    1440
accaggactg gctgaatggc aaggagtaca agtgcaaggt ctccaacaaa gccctcccag    1500
cccccatcga gaaaaccatc tccaaagcca aggtgggac ccgtgggggtg cgagggccac    1560 atggacagag gccggctcgg cccacccttct gccctgagag tgaccgctgt accaacctct    1620
gtccctacag ggcagccccg agaaccacag gtgtacaccc tgcccccatc ccgggatgag    1680
ctgaccaaga accaggtcag cctgacctgc ctggtcaaag gcttctatcc cagcgacatc    1740
gccgtggagt gggagagcaa tgggcagccg gagaacaact acaagaccac gcctcccgtg    1800
ctggactccg acggctcctt cttcctctac agcaagctca ccgtggacaa gagcaggtgg    1860
cagcagggga acgtcttctc atgctccgtg atgcatgagg ctctgcacaa ccactacaca    1920
cagaagagcc tctccctgtc tccgggtaaa taatga                              1956

<210> SEQ ID NO 11
<211> LENGTH: 218
<212> TYPE: PRT
<213> ORGANISM: Artificial Sequence
<220> FEATURE:
<223> OTHER INFORMATION: Synthetically Generated Sequence

<400> SEQUENCE: 11

Asp Ile Val Leu Thr Gln Ser Pro Ala Thr Leu Ser Val Ser Pro Gly
1               5                   10                  15

Glu Arg Ala Thr Ile Ser Cys Arg Ala Ser Gln Lys Val Ser Ser Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Gln His Ser Trp
                85                  90                  95

Glu Ile Pro Pro Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205
```

Val Thr Lys Ser Phe Asn Arg Gly Glu Cys
    210                 215

<210> SEQ ID NO 12
<211> LENGTH: 660
<212> TYPE: DNA
<213> ORGANISM: Artificial Sequence
<220> FEATURE:
<223> OTHER INFORMATION: Synthetically Generated Sequence

<400> SEQUENCE: 12

```
gacatcgtgc tgacccagtc ccccgccacc ctgtccgtgt cccccggcga gagggccacc    60
atctcctgca gggcctccca gaaggtgtcc tcctccacct actcctacat gcactggtac   120
cagcagaagc ccggccagcc ccccaagctg ctgatcaagt acgcctccaa cctggagtcc   180
ggcgtgcccg ccaggttctc cggctccggc tccggcaccg acttcaccct gaccatctcc   240
tccgtggagc ccgaggactt cgccacctac tactgccagc actcctggga tccccccccc   300
accttcggcg gcggcaccaa gctggaaatc aaacgtacgg tggctgcacc atctgtcttc   360
atcttcccgc catctgatga gcagttgaaa tctggaactg cctctgttgt gtgcctgctg   420
aataacttct atcccagaga ggccaaagta cagtggaagg tggataacgc cctccaatcg   480
ggtaactccc aggagagtgt cacagagcag gacagcaagg acagcaccta cagcctcagc   540
agcaccctga cgctgagcaa agcagactac gagaaacaca agtctacgc ctgcgaagtc   600
acccatcagg gcctgagctc gcccgtcaca aagagcttca caggggaga gtgttagtga   660
```

<210> SEQ ID NO 13
<211> LENGTH: 448
<212> TYPE: PRT
<213> ORGANISM: Artificial Sequence
<220> FEATURE:
<223> OTHER INFORMATION: Synthetically Generated Sequence

<400> SEQUENCE: 13

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

Lys Ser Lys Ala Thr Leu Thr Val Asp Arg Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser

```
                180                185                190
Ser Leu Gly Thr Gln Thr Tyr Ile Cys Asn Val Asn His Lys Pro Ser
            195                200                205
Asn Thr Lys Val Asp Lys Val Glu Pro Lys Ser Ser Asp Lys Thr
        210                215                220
His Thr Ser Pro Pro Ser Pro Ala Pro Glu Leu Leu Gly Gly Ser Ser
225                230                235                240
Val Phe Leu Phe Pro Pro Lys Pro Lys Asp Thr Leu Met Ile Ser Arg
                245                250                255
Thr Pro Glu Val Thr Cys Val Val Val Asp Val Ser His Glu Asp Pro
            260                265                270
Glu Val Lys Phe Asn Trp Tyr Val Asp Gly Val Glu Val His Asn Ala
        275                280                285
Lys Thr Lys Pro Arg Glu Glu Gln Tyr Asn Ser Thr Tyr Arg Val Val
    290                295                300
Ser Val Leu Thr Val Leu His Gln Asp Trp Leu Asn Gly Lys Glu Tyr
305                310                315                320
Lys Cys Lys Val Ser Asn Lys Ala Leu Pro Ala Pro Ile Glu Lys Thr
                325                330                335
Ile Ser Lys Ala Lys Gly Gln Pro Arg Glu Pro Gln Val Tyr Thr Leu
            340                345                350
Pro Pro Ser Arg Asp Glu Leu Thr Lys Asn Gln Val Ser Leu Thr Cys
        355                360                365
Leu Val Lys Gly Phe Tyr Pro Ser Asp Ile Ala Val Glu Trp Glu Ser
    370                375                380
Asn Gly Gln Pro Glu Asn Asn Tyr Lys Thr Thr Pro Pro Val Leu Asp
385                390                395                400
Ser Asp Gly Ser Phe Phe Leu Tyr Ser Lys Leu Thr Val Asp Lys Ser
                405                410                415
Arg Trp Gln Gln Gly Asn Val Phe Ser Cys Ser Val Met His Glu Ala
            420                425                430
Leu His Asn His Tyr Thr Gln Lys Ser Leu Ser Leu Ser Pro Gly Lys
        435                440                445

<210> SEQ ID NO 14
<211> LENGTH: 1956
<212> TYPE: DNA
<213> ORGANISM: Artificial Sequence
<220> FEATURE:
<223> OTHER INFORMATION: Synthetically Generated Sequence

<400> SEQUENCE: 14
caggtgcagc tggtgcagtc cggcgccgag gtggtgaagc ccggcgcctc cgtgaagctg      60
tcctgcaagg cctccggcta catcttcacc tcctactaca tgtactgggt gaagcaggcc     120
cccggccagg gcctggagtg gatcggcgag atcaacccct ccaacggcga caccaacttc     180
aacgagaagt tcaagtccaa ggccaccctg accgtggaca ggtccgcctc caccgcctac     240
atggagctgt cctccctgag gtccgaggac accgccgtgt actactgcac caggtccgac     300
ggcaggaacg acatggactc ctggggccag ggcaccctgg tgaccgtgtc ctccgctagc     360
accaagggcc catcggtctt ccccctggca ccctcctcca agagcacctc tgggggcaca     420
gcagccctgg gctgcctggt caaggactac ttccccgaac cggtgacggt gtcgtggaac     480
tcaggcgccc tgaccagcgg cgtgcacacc ttccggctgt cctacagtc ctcaggactc     540 tactccctca gcagcgtggt gaccgtgccc tccagcagct gggcacccca gacctacatc     600
```

-continued

```
tgcaacgtga atcacaagcc cagcaacacc aaggtggaca agaaagttgg tgagaggcca      660
gcacagggag ggagggtgtc tgctggaagc caggctcagc gctcctgcct ggacgcatcc      720
cggctatgca gccccagtcc agggcagcaa ggcaggcccc gtctgcctct tcacccggag      780
gcctctgccc gccccactca tgctcaggga gagggtcttc tggcttttc cccaggctct       840 gggcaggcac aggctaggtg cccctaaccc aggccctgca cacaaggggg caggtgctgg      900
gctcagacct gccaagagcc atatccggga ggacctgcc cctgacctaa gcccacccca       960
aaggccaaac tctccactcc ctcagctcgg acaccttctc tcctcccaga ttccagtaac     1020
tcccaatctt ctctctgcag agcccaaatc tagtgacaaa actcacacaa gcccaccgag     1080
cccaggtaag ccagcccagg cctcgccctc cagctcaagg cgggacaggt gccctagagt     1140
agcctgcatc cagggacagg ccccagccgg gtgctgacac gtccacctcc atctcttcct     1200
cagcacctga actcctgggg ggatcctcag tcttcctctt cccccaaaa cccaaggaca      1260 ccctcatgat ctcccggacc cctgaggtca catgcgtggt ggtggacgtg agccacgaag     1320
accctgaggt caagttcaac tggtacgtgg acggcgtgga ggtgcataat gccaagacaa     1380
agccgcggga ggagcagtac aacagcacgt accgtgtggt cagcgtcctc accgtcctgc     1440
accaggactg gctgaatggc aaggagtaca agtgcaaggt ctccaacaaa gccctcccag     1500
cccccatcga gaaaccatc tccaaagcca aggtgggac ccgtggggtg cgagggccac       1560
atggacagag gccggctcgg cccaccctct gccctgagag tgaccgctgt accaacctct     1620
gtccctacag ggcagccccg agaaccacag gtgtacaccc tgcccccatc ccgggatgag     1680
ctgaccaaga accaggtcag cctgacctgc ctggtcaaag gcttctatcc cagcgacatc     1740
gccgtggagt gggagagcaa tgggcagccg gagaacaact acaagaccac gcctcccgtg     1800
ctggactccg acggctcctt cttcctctac agcaagctca ccgtggacaa gagcaggtgg     1860
cagcagggga acgtcttctc atgctccgtg atgcatgagg ctctgcacaa ccactacaca     1920
cagaagagcc tctccctgtc tccgggtaaa taatga                                1956
```

<210> SEQ ID NO 15
<211> LENGTH: 18
<212> TYPE: PRT
<213> ORGANISM: Artificial Sequence
<220> FEATURE:
<223> OTHER INFORMATION: Synthetically Generated Sequence

<400> SEQUENCE: 15

Ile Ser Cys Arg Ala Ser Gln Arg Val Ser Ser Thr Tyr Ser Tyr
1               5                   10                  15
Met His

<210> SEQ ID NO 16
<211> LENGTH: 7
<212> TYPE: PRT
<213> ORGANISM: Artificial Sequence
<220> FEATURE:
<223> OTHER INFORMATION: Synthetically Generated Sequence

<400> SEQUENCE: 16

Tyr Ala Ser Asn Leu Glu Ser
1               5

<210> SEQ ID NO 17
<211> LENGTH: 9
<212> TYPE: PRT

<213> ORGANISM: Artificial Sequence
<220> FEATURE:
<223> OTHER INFORMATION: Synthetically Generated Sequence

<400> SEQUENCE: 17

Gln His Ser Trp Glu Ile Pro Pro Thr
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetically Generated Sequence

<400> SEQUENCE: 18

Ser Tyr Tyr Met Tyr
1               5

<210> SEQ ID NO 19
<211> LENGTH: 17
<212> TYPE: PRT
<213> ORGANISM: Artificial Sequence
<220> FEATURE:
<223> OTHER INFORMATION: Synthetically Generated Sequence

<400> SEQUENCE: 19

Glu Ile Asn Pro Ser Asn Gly Asp Thr Asn Phe Asn Glu Lys Phe Lys
1               5                   10                  15
Ser

<210> SEQ ID NO 20
<211> LENGTH: 9
<212> TYPE: PRT
<213> ORGANISM: Artificial Sequence
<220> FEATURE:
<223> OTHER INFORMATION: Synthetically Generated Sequence

<400> SEQUENCE: 20

Ser Asp Gly Arg Asn Asp Met Asp Ser
1               5

<210> SEQ ID NO 21
<211> LENGTH: 448
<212> TYPE: PRT
<213> ORGANISM: Artificial Sequence
<220> FEATURE:
<223> OTHER INFORMATION: Synthetically Generated Sequence

<400> SEQUENCE: 21

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr

```
            100                 105                 110
Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 22
<211> LENGTH: 374
<212> TYPE: PRT
<213> ORGANISM: Homo sapiens

<400> SEQUENCE: 22

Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30
```

```
Val Phe Gln Glu Glu Thr Val Thr Leu His Cys Glu Val Leu His Leu
         35                  40                  45

Pro Gly Ser Ser Thr Gln Trp Phe Leu Asn Gly Thr Ala Thr Gln
 50                  55                  60

Thr Ser Thr Pro Ser Tyr Arg Ile Thr Ser Ala Ser Val Asn Asp Ser
 65                  70                  75                  80

Gly Glu Tyr Arg Cys Gln Arg Gly Leu Ser Gly Arg Ser Asp Pro Ile
                 85                  90                  95

Gln Leu Glu Ile His Arg Gly Trp Leu Leu Leu Gln Val Ser Ser Arg
             100                 105                 110

Val Phe Thr Glu Gly Glu Pro Leu Ala Leu Arg Cys His Ala Trp Lys
         115                 120                 125

Asp Lys Leu Val Tyr Asn Val Leu Tyr Tyr Arg Asn Gly Lys Ala Phe
 130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
        275                 280                 285

Val Trp Phe His Val Leu Phe Tyr Leu Ala Val Gly Ile Met Phe Leu
    290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
                325                 330                 335

Val Ile Ser Ser Leu Gln Glu Asp Arg His Leu Glu Glu Glu Leu Lys
            340                 345                 350

Cys Gln Glu Gln Lys Glu Glu Gln Leu Gln Glu Gly Val His Arg Lys
        355                 360                 365

Glu Pro Gln Gly Ala Thr
    370

<210> SEQ ID NO 23
<211> LENGTH: 317
<212> TYPE: PRT
<213> ORGANISM: Homo sapiens

<400> SEQUENCE: 23

Met Thr Met Glu Thr Gln Met Ser Gln Asn Val Cys Pro Arg Asn Leu
1               5                   10                  15

Trp Leu Leu Gln Pro Leu Thr Val Leu Leu Leu Leu Ala Ser Ala Asp
                20                  25                  30
```

```
Ser Gln Ala Ala Pro Pro Lys Ala Val Leu Lys Leu Glu Pro Pro
        35                  40                  45

Trp Ile Asn Val Leu Gln Glu Asp Ser Val Thr Leu Thr Cys Gln Gly
    50                  55                  60

Ala Arg Ser Pro Glu Ser Asp Ser Ile Gln Trp Phe His Asn Gly Asn
65                  70                  75                  80

Leu Ile Pro Thr His Thr Gln Pro Ser Tyr Arg Phe Lys Ala Asn Asn
                85                  90                  95

Asn Asp Ser Gly Glu Tyr Thr Cys Gln Thr Gly Gln Thr Ser Leu Ser
                100                 105                 110

Asp Pro Val His Leu Thr Val Leu Ser Glu Trp Leu Val Leu Gln Thr
                115                 120                 125

Pro His Leu Glu Phe Gln Glu Gly Glu Thr Ile Met Leu Arg Cys His
            130                 135                 140

Ser Trp Lys Asp Lys Pro Leu Val Lys Val Thr Phe Phe Gln Asn Gly
145                 150                 155                 160

Lys Ser Gln Lys Phe Ser His Leu Asp Pro Thr Phe Ser Ile Pro Gln
                    165                 170                 175

Ala Asn His Ser His Ser Gly Asp Tyr His Cys Thr Gly Asn Ile Gly
                180                 185                 190

Tyr Thr Leu Phe Ser Ser Lys Pro Val Thr Ile Thr Val Gln Val Pro
            195                 200                 205

Ser Met Gly Ser Ser Ser Pro Met Gly Ile Ile Val Ala Val Val Ile
    210                 215                 220

Ala Thr Ala Val Ala Ala Ile Val Ala Ala Val Val Ala Leu Ile Tyr
225                 230                 235                 240

Cys Arg Lys Lys Arg Ile Ser Ala Asn Ser Thr Asp Pro Val Lys Ala
                    245                 250                 255

Ala Gln Phe Glu Pro Pro Gly Arg Gln Met Ile Ala Ile Arg Lys Arg
                260                 265                 270

Gln Leu Glu Glu Thr Asn Asn Asp Tyr Glu Thr Ala Asp Gly Gly Tyr
            275                 280                 285

Met Thr Leu Asn Pro Arg Ala Pro Thr Asp Asp Asp Lys Asn Ile Tyr
        290                 295                 300

Leu Thr Leu Pro Pro Asn Asp His Val Asn Ser Asn Asn
305                 310                 315

<210> SEQ ID NO 24
<211> LENGTH: 254
<212> TYPE: PRT
<213> ORGANISM: Homo sapiens

<400> SEQUENCE: 24

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
```

-continued

```
                    85                  90                  95
Ser Asp Pro Val Gln Leu Glu Val His Ile Gly Trp Leu Leu Leu Gln
                100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 25
<211> LENGTH: 233
<212> TYPE: PRT
<213> ORGANISM: Homo sapiens

<400> SEQUENCE: 25

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Ser Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
        195                 200                 205
```

-continued

```
Val Ser Phe Cys Leu Val Met Val Leu Leu Phe Ala Val Asp Thr Gly
    210                 215                 220

Leu Tyr Phe Ser Val Lys Thr Asn Ile
225                 230
```

ANTI-CD40L ANTIBODIES

CROSS REFERENCE TO RELATED APPLICATIONS

This application is a Divisional of U.S. application Ser. No. 16/125,317 filed on Sep. 7, 2018, which is a Divisional of U.S. application Ser. No. 15/667,477 filed on Aug. 2, 2017, which is a Continuation application of, and claims priority to, PCT International Application No. PCT/US2016/016165, filed Feb. 2, 2016, which claims the benefit under 35 USC § 119 of U.S. Provisional Application No. 62/111,261, filed Feb. 3, 2015, the entire contents of the aforementioned disclosures are hereby incorporated by reference.

FIELD

Anti-CD40L antibodies, compositions comprising the antibodies, and method of using same for treatment of CD40L-related diseases or disorders.

SEQUENCE LISTING

This application contains a Sequence Listing which is submitted herewith in electronically readable format. The electronic Sequence Listing file was created on May 28, 2020, is named "224823-467762_Amended_2020-05-28 ST25.txt" and has a size of 43 KB. The entire contents of the Sequence Listing in the electronic "224823-467762_Amended_2020-05-28_ST25.txt" file are incorporated herein by this reference.

BACKGROUND

The interaction of CD40 with its ligand CD40L plays a critical role in regulating immune responses. Binding of CD40L to CD40 triggers activation of the CD40 pathway which up-regulates costimulatory molecules such as CD80 and CD86. Blockade of the interaction between CD40 and CD40L by monoclonal antibodies has been shown to result in protection from autoimmunity and graft rejection in various preclinical models. Recently, in a mouse model of amyotrophic lateral sclerosis, an antibody directed to CD40L was shown to delay disease onset and prolong survival the onset of disease. (U.S. Pat. No. 8,435,514, hereby incorporated by reference). In early clinical studies, the humanized anti-CD40L antibody hu5c8 showed efficacy in patients with lupus and in patients with immune thrombocytopenic purpura. However, incidents of thromboembolism in the patients treated with hu5c8 halted further trials. Further in vitro and preclinical animal studies established that interaction of the Fc with the Fc receptor FcγRIIa caused platelet activation, and aggregation, that resulted in thromboembolic events. Various approaches have been taken to reduce or eliminate the interaction of the immunoglobulin Fc region with FcγRIIa, including introducing a point mutation in the Fc region to make an aglycosylated anti-IC40L IgG1 which lacked Fc effector function. Other approaches use fragments of antibodies lacking the Fc region or antibodies that contain multiple amino acid substitutions in the Fc region. Although the anti-CD40L antibody, hu5c8, showed efficacy in human patients there is no anti-CD40L antibody on the market. Accordingly, there is a need for improved anti-CD40L antibodies for administration to humans that do not cause platelet activation or aggregation yet are stable and bind to CD40L.

SUMMARY

The present invention provides anti-CD40L antibodies, suitable for use in humans and non-human primates, having an Fc domain that has been engineered to reduce or eliminate platelet aggregation and the concomitant risk of thromboembolism. In one aspect of the invention, the present invention provides antibodies that are humanized versions of the mouse anti-human CD40L antibody 5c8. In one embodiment an antibody of the present invention comprises a human IgG1 consensus framework wherein the variable light chain and the variable heavy chain comprise the CDR sequences of 5c8.

One aspect of the present invention is an isolated antibody that binds to CD40L and that comprises a light chain and a heavy chain, wherein (i) the light chain comprises a light chain variable region comprising an amino acid sequence having at least 95% sequence identity with SEQ ID NO:1; (ii) the heavy chain comprises a heavy chain variable region and an Fc region wherein a) the heavy chain variable region comprises an amino acid sequence having at least 95% sequence identity with SEQ ID NO:2; and b) the Fc region comprises an amino acid sequence having at least 95% sequence identity with SEQ ID NO:3 wherein the Fc region comprises one or a combination of substitutions selected from the group consisting of C11S, C14S, and P23S. Optionally the Fc region comprises a further amino acid substitution C5S.

Another aspect of the present invention is a method for treating a subject with a CD40L-associated disease or disorder comprising administering to the subject a therapeutically effective amount of an antibody according to the invention. One embodiment of the present invention is a method for treating a subject with a neurodegenerative or neuromuscular disease or disorder; an inflammatory or immune disease or disorder; or an autoimmune disease, comprising administering to the subject a therapeutically effective amount of an antibody according to the invention. Another embodiment is a method for treating a subject with a CD40L-associated disease or disorder comprising administering to the subject a therapeutically effective amount of an antibody according to the invention administered in combination with a compound that blocks the interaction between CD28 and CD86 or between CD28 and CD80.

BRIEF DESCRIPTION OF THE FIGURES

FIGS. 1A, 1B and 1C show the heavy chain amino acid sequences for hu5c8 (SEQ ID NO:21) (FIG. 1A), JB5 (SEQ ID NO:9) (FIG. 1B) and JB5-K74R (SEQ ID NO:13) (FIG. 1C). The amino acids shown in bold type indicate amino acids that differ between the heavy chain sequences for 5c8 and the heavy chain sequences for JB5 and JB5-K74R.

FIGS. 2A-2D show the light chain amino acid sequence for JB5 (SEQ ID NO:7) (FIG. 2A), the light chain amino acid sequence for JB5-R28K (SEQ ID NO:11) (FIG. 2B), the Fc region amino acid sequence for hu5c8 (SEQ ID NO:3) (FIG. 2C), and the Fc region amino acid sequence for JB5 (SEQ ID NO:4) (FIG. 2D). The amino acids shown in bold type indicate the amino acids that differ between the light chain sequences for 5c8 and JB5-R28K and between the Fc regions for hu5c8 and JB5.

FIG. 15 provides the variable light region amino acid sequence of the anti-CD40L antibodies JB5 and hu5c8 (SEQ ID NO:1), the variable heavy region amino acid sequence of the anti-CD40L antibodies JB5 and hu5c8 (SEQ ID NO:2), the Fc region amino acid sequence of the anti-CD40L antibody hu5c8 (SEQ ID NO:3), the Fc region amino acid sequence of the anti-CD40L antibody JB5 (SEQ ID NO:4), the variable light region amino acid sequence of the anti-CD40L antibody JB5-R28K (SEQ ID NO:5), the variable heavy region amino acid sequence of the anti-CD40L antibody JB5-K74R (SEQ ID NO:6), and the light chain amino acid sequence of the anti-CD40L antibody JB5 (SEQ ID NO:7).

FIG. 16 provides the light chain synthetic nucleotide sequence that encodes the anti-CD40L antibody JB5 (SEQ ID NO:8), upper case letters represent the exons and the lower case letters represent the intron sequences of the synthetic gene, and also provides the heavy chain amino acid sequence of the anti-CD40L antibody JB5 (SEQ ID NO:9).

FIG. 17 provides a synthetic nucleic acid sequence that encodes the heavy chain of the anti-CD40L antibody JB5 (SEQ ID NO:10), upper case letters represent the exons and the lower case letters represent the intron sequences of the synthetic gene.

FIG. 18 provides the amino acid sequence of the anti-CD40L antibody JB5-R28K (SEQ ID NO:11), a synthetic nucleic acid sequence that encodes the light chain of the anti-CD40L antibody JB5-R28K (SEQ ID NO:12), upper case letters represent the exons and the lower case letters represent the intron sequences of the synthetic gene, and also provides the heavy chain amino acid sequence of the anti-CD40L antibody JB5-K74R (SEQ ID NO:13).

FIG. 19 provides a synthetic nucleic acid sequence that encodes the heavy chain of the anti-CD40L antibody JB5-K74R (SEQ ID NO:14) upper case letters represent the exons and the lower case letters represent the intron sequences of the synthetic gene.

FIG. 20 provides the amino acid sequences of the CDRs of the heavy and light chain of the anti-CD40L antibody JB5: JB5 CDR-L1 (SEQ ID NO:15), JB5 CDR-L2 (SEQ ID NO:16), JB5 CDR-L3 (SEQ ID NO:17), JB5 CDR-H1 (SEQ ID NO:18), JB5 CDR-H2 (SEQ ID NO:19), JB5 CDR-H3 (SEQ ID NO:20) and the amino acid sequence of the hu5C8 heavy chain (SEQ ID NO: 21).

DETAILED DESCRIPTION

Definitions

Figure 3:
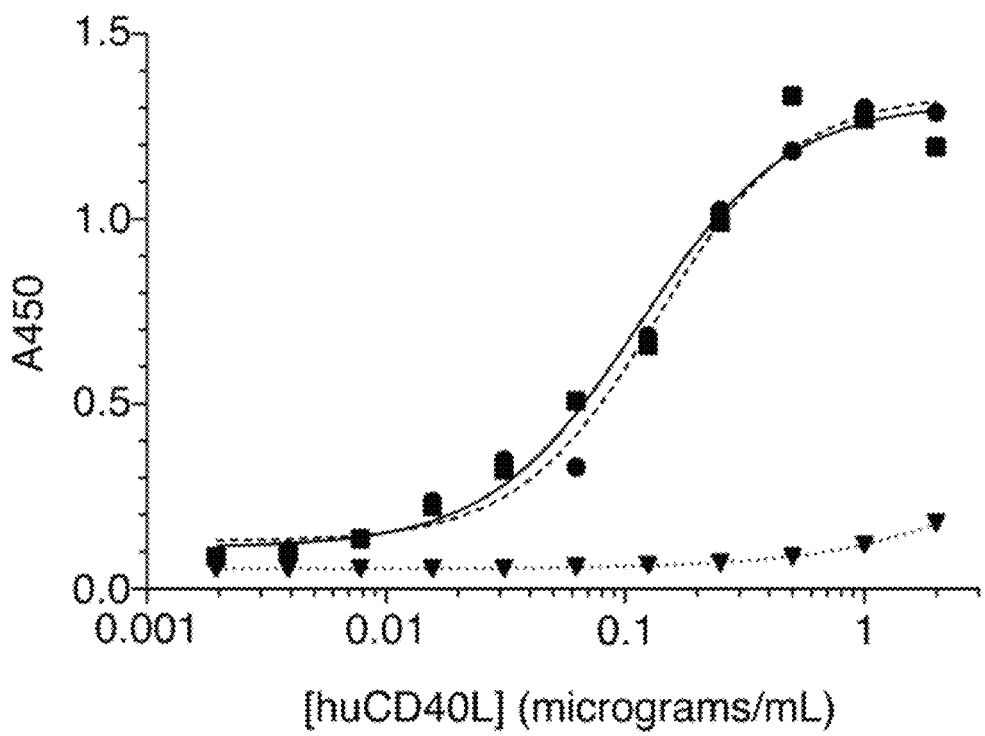
FIG. 3 is a graph showing the relative binding to human CD40L, of JB5 antibody (circles, dotted line), hu5c8 antibody (squares-solid line), and the control CTLA4-IgG1 (triangles).

The terms such as "comprises", "comprised", "comprising", "contains", "containing" and the like have the meaning attributed in United States patent law; these terms are inclusive or open-ended and do not exclude additional, unrecited elements or method steps. Terms such as "consisting essentially of" and "consists essentially of" have the meaning attributed to them in United States patent law; these terms allow for the inclusion of additional ingredients or steps that do not materially affect the basic and novel characteristics of the claim invention. The terms "consists of" and "consisting of" have the meaning ascribed to them in United States patent law; these terms are close ended.

The terms "treat," "treatment" and the like, include therapeutic treatment and prophylactic treatment. Therapeutic treatment is treatment of a subject that has signs or symptoms of the disease, condition or disorder to be treated. Prophylactic treatments refers to treatment of a subject that is predisposed to the disease, condition or disorder that does not show overt signs of the disease, condition or disorder. Thus, treatment may result in stasis of, partial or total alleviation, or reduction of signs or symptoms of illness, and specifically includes, without limitation, prolongation of survival.

About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range.

The use of the conjunction "or" is used interchangeably with at "least one of". For example: where a composition comprises A or B, the method must comprise at least one of A and B but may also comprise both A and B. Likewise a composition comprising "A, B, C or D" must comprise at least one of the group of A, B, C and D, but may also comprise all or any combination of A, B, C and D.

Amino acid substitutions are denoted by the convention in which the original amino acid, the position of the amino acid in the specified sequence and the replacement amino acid are identified, for example, C11S would indicate that the cysteine at position 11 of the polypeptide sequence is replaced with a serine.

"5c8" refers to the mouse anti-human antibody that binds CD40L and is produced by the hybridoma that is available from the ATCC having the accession number HB10916 and is described in U.S. Pat. No. 5,474,771. "hu5c8" refers to a humanized version of 5c8 the sequence of which is disclosed in Karpusas, et al., Structure vol. 9, pp 321-329, (2001).

Reference in the specification is made to percent identity between polypeptide or amino acid sequences. The percent identity between the two sequences is a function of the number of identical positions shared by the sequences, taking into account the number of gaps, and the length of each gap, which need to be introduced for optimal alignment of the two sequences. Identity can be measured as "local identity" or "global identity". Local identity refers the degree of sequence relatedness between polypeptides as determined by the match between strings of such sequences. Global identity refers to the degree of sequence relatedness of a polypeptide compared to the full-length of a reference polypeptide. Unless specified otherwise, as used herein, identity means global identity. For the purposes of this disclosure, the percentages for global identity are calculated using Needleman and Wunsch ((1970) J. Mol. Biol. 48:444-453) algorithm using a Blossum 62 scoring matrix with a gap penalty of 12, a gap extend penalty of 4, and a frameshift gap penalty of 5. There are many publically available software programs that incorporate the Needleman and Wunsch algorithm, e.g. the GAP program in the GCG software package.

CD40L is also known as CD154, gp39, T-BAM, 5c8 antigen, or TNF related activation protein (TRAP).

EMBODIMENTS

The present invention provides for therapeutic anti-human CD40L antibodies and methods for using the antibodies of the invention for treating patients with a CD40L-associated disease or disorder. Various exemplary embodiments of the present invention are provided, however, the invention is to be limited by the claims and not the disclosed embodiments.

In one aspect of the invention, the present invention provides antibodies that are modified versions of the anti-CD40L antibody hu5c8 that comprise a human IgG1 consensus framework having the variable light chain and the variable heavy chain CDR sequences of hu5c8 with an Fc domain modified to prevent platelet activation.

Table 1 provides a description of the SEQ ID NOs referenced in the application.

TABLE 1

| SEQ ID NO: | Description of Sequence |
|---|---|
| 1 | Light chain variable region amino acid sequence (hu5c8 and JB5) |
| 2 | Heavy chain variable region amino acid sequence (hu5c8 and JB5) |
| 3 | Fc region amino acid sequence (hu5c8) |
| 4 | JB5 Fc region amino acid sequence |
| 5 | JB5-R28K light chain variable region amino acid sequence |
| 6 | JB5-K74R heavy chain variable region amino acid sequence |
| 7 | JB5 light chain amino acid sequence |
| 8 | JB5 light chain nucleic acid sequence |
| 9 | JB5 heavy chain amino acid sequence |

TABLE 1-continued

| SEQ ID NO: | Description of Sequence |
|---|---|
| 10 | JB5 heavy chain nucleic acid sequence |
| 11 | JB5-R28K light chain amino acid sequence |
| 12 | JB5-R28K light chain synthetic gene nucleic acid sequence |
| 13 | JB5-K74R heavy chain amino acid sequence |
| 14 | JB5-K74R heavy chain synthetic gene nucleic acid sequence |
| 15 | CDR-1 of the JB5 Variable Light Chain amino acid sequence |
| 16 | CDR-2 of the JB5 Variable Light Chain amino acid sequence |
| 17 | CDR-3 of the JB5 Variable Light Chain amino acid sequence |
| 18 | CDR-1 of the JB5 Variable Heavy Chain amino acid sequence |
| 19 | CDR-2 of the JB5 Variable Heavy Chain amino acid sequence |
| 20 | CDR-3 of the JB5 Variable Heavy Chain amino acid sequence |
| 21 | Hu5c8 Heavy Chain amino acid sequence |

One embodiment (embodiment A) is an isolated antibody that binds to CD40L and that comprises a light chain and a heavy chain, wherein the light chain comprises a light chain variable region comprising an amino acid sequence having at least 90%, or at least 91%, or at least 92%, or at least 93%, or at least 94%, or at least 95%, or at least 96% or at least 97%, or at least 98% or at least 99% sequence identity with SEQ ID NO: 1 and the heavy chain comprises a variable heavy chain region and an Fc region, wherein the heavy chain variable region comprises an amino acid sequence having at least 90%, or at least 91%, or at least 92%, or at least 93%, or at least 94%, or at least 95%, or at least 96%, or at least 97%, or at least 98%, or at least 99% sequence identity with SEQ ID NO:2 and the Fc region comprises an amino acid sequence having at least at least 90%, or at least 91%, or at least 92%, or at least 93%, or at least 94%, or at least 95%, or at least 96%, or at least 97%, or at least 98%, or at least 99% sequence identity with SEQ ID NO: 3 wherein the Fc region comprises one or a combination of substitutions selected from the group consisting of C11S, C14S, and P23S.

Another embodiment (embodiment B) is an isolated antibody according to embodiment A, wherein the Fc region further comprises the amino acid substitution C5S.

In variations of the embodiments A and B the antibody comprises a light chain variable region that does not comprise any of the substitutions T33W, S26D, and Q27E.

In other variations of embodiments A and B, the light chain variable region comprises the substitution R28K.

In some variations of the embodiments of A and B, the CDRs of the heavy and light chain have the sequences listed in Table 2.

TABLE 2

| CDR1 light chain | ISCRASQRVSSSTYSYMH (SEQ ID NO: 15) |
|---|---|
| CDR2 light chain | YASNLES (SEQ ID NO: 16) |
| CDR3 light chain | QHSWEIPPT (SEQ ID NO: 17) |
| CDR1 heavy chain | SYYMY (SEQ ID NO: 18) |
| CDR2 heavy chain | EINPSNGDTNFNEKFKS (SEQ ID NO: 19) |
| CDR3 heavy chain | SDGRNDMDS (SEQ ID NO: 20) |

In yet other variation of embodiments A and B, the light chain variable region comprises the amino acid sequence ICRRASQRVSSSTYSYMH (SEQ ID NO:15). In still other embodiments, the light chain variable region comprises the amino acid sequence ICRRASQRVSSSTYSYMH (SEQ ID NO:15) and one or both of the amino acid sequences YASNLES (SEQ ID NO:16) and QHSWEIPPT (SEQ ID NO:17).

In some variations of embodiments A and B, the light chain variable region comprises the amino acid sequence of SEQ ID NO:1. In yet other embodiments the light chain variable region consists of the amino acid of SEQ ID NO:1. In some embodiments, the light chain consists essentially of the amino acid sequence of SEQ ID NO:7. In other embodiments, the light chain consists of the amino acid sequence of SEQ ID NO:7. In still other embodiments, the light chain comprises the amino acid sequence of SEQ ID NO:11. In yet other embodiments, the light chain consists essentially of the amino acid sequence of SEQ ID NO:11. In still other embodiments, the light chain consists of the amino acid sequence of SEQ ID NO:11.

In other variations of the embodiments A and B, the antibody comprises a heavy chain variable region that does not comprise any of the substitutions T30H, Y33W, or S54N. In some embodiments of the antibodies of embodiments A and B, the light chain variable region does not comprise any of the substitutions T33W, S26D, and Q27E. In other variations of embodiments A and B, the light chain variable region does not comprise any of the substitutions T33W, S26D, and Q27E and the heavy chain variable region does not comprise any of the substitutions T30H, Y33W, or S54N.

In yet other variations of the embodiments A and B, the heavy chain variable region comprises the substitution K74R. In one embodiment the heavy chain variable region comprises one or any combination of the amino acid sequences SYYMY (SEQ ID NO:18), EINPSNGDTNFNEKFKS (SEQ ID NO:19), and SDGRNDMDS (SEQ ID NO:20).

In another embodiment, the heavy chain variable region comprises the amino acid sequence of SEQ ID NO:2. In yet another embodiment the heavy chain variable region consists essentially of the amino acid sequence of SEQ ID NO:2. In still another embodiment the heavy chain variable region consists of the amino acid sequence of SEQ ID NO:2. In some embodiments, the heavy chain variable region comprises the amino acid sequence of SEQ ID NO:6. In yet other embodiments the heavy chain variable region consists essentially of the amino acid sequence of SEQ ID NO:6. In still other embodiments the heavy chain variable region consists of the amino acid sequence of SEQ ID NO:6.

One embodiment of the present invention is an isolated antibody, wherein the light chain comprises the amino acid sequence of SEQ ID NO:1 and the heavy chain consists of the amino acid sequence of SEQ ID NO:9.

Another embodiment of the present invention is an isolated antibody, wherein the light chain consists of the amino acid sequence of SEQ ID NO:7 and the heavy chain consists of the amino acid sequence of SEQ ID NO:9.

Yet another embodiment is an isolated antibody wherein the light chain variable region comprises the amino acid sequence of SEQ ID NO:5 and the heavy chain consists of the amino acid sequence of SEQ ID NO:9.

Still another embodiment is an isolated antibody wherein the light chain consists of the amino acid sequence of SEQ ID NO:11 and the heavy chain consists of the amino acid sequence of SEQ ID NO:9.

Yet another embodiment, is an isolated antibody wherein the light chain consists of the amino acid sequence of SEQ ID NO:7 and the heavy chain consists of the amino acid sequence of SEQ ID NO:13.

Another embodiment is an isolated antibody wherein the light chain consists of the amino acid sequence of SEQ ID NO:11 and the heavy chain consists of the amino acid sequence of SEQ ID NO:13.

In preferred embodiments, the antibody of the present invention is stable at 37° C. for a period of at least 12 hours.

In another aspect, the present disclosure provides methods for treating subjects having a CD40L-associated disease or disorder comprising administering to the subject a therapeutically effective amount of an antibody of the present invention. It is contemplated that an antibody of the invention, or mixtures thereof, can be administered to the subject as a monotherapy, which, as used herein, means that the antibody is the only therapeutic agent administered to the patient that is directed to the treatment of the underlying disease or disorder. Monotherapy using an antibody of the invention does not preclude the administration of other drugs, non-limiting examples of which are muscle relaxants, nonsteroidal anti-inflammatory drugs, pain medications, and antidepressants. Accordingly, in various embodiments of the invention, one or a mixture of the antibodies of the invention, is the sole therapeutic agent directed to treatment of the underlying disease or disorder.

It is also contemplated that the antibodies of the invention, or mixtures thereof, can be administered in combination with other therapeutic agents. "In combination with" includes, but is not limited to, administration of the therapeutic agents at different times, at different frequencies, simultaneously, or combined in a single dosage form.

One embodiment is a method for treating a subject with a neurodegenerative or neuromuscular disease or disorder comprising administering to the subject a therapeutically effective amount of an antibody of the present invention. Neurodegenerative or neuromuscular diseases and disorders include, but are not limited to, Alzheimer's Disease, Parkinson's Disease, Amyotrophic Lateral Sclerosis, Multifocal Motor Neuropathy, Primary Lateral Sclerosis, Spinal Muscular Atrophy, Kennedy's Disease, and Spinocerebellar Ataxia.

Another embodiment is a method for treating a subject with Amyotrophic Lateral Sclerosis comprising administering to the subject a therapeutically effective amount of an antibody of the present invention.

One embodiment of the present invention is a method for treating a subject with an inflammatory or immune disease or disorder comprising administering to the subject a therapeutically effective amount of an antibody of the present invention. Inflammatory or immune diseases and disorders include, but are not limited to, colitis, drug induced lupus nephritis, graft versus host disease, transplant rejection and atherosclerosis.

Still another embodiment is a method for treating a subject having an autoimmune disease comprising administering to the subject a therapeutically effective amount of an antibody of the present invention. Autoimmune diseases include, but are not limited to systemic lupus erythematous, type-1 diabetes, myasthenia gravis, inflammatory bowel disease, immune thrombocytopenic purpura and rheumatoid arthritis.

Yet another embodiment is method of inhibiting an immune response in a subject comprising administering to the subject a therapeutically effective amount of an antibody of the present invention. In one embodiment the immune response is graft vs. host disease. In another embodiment the immune response is organ transplant rejection.

In some embodiments, an antibody of the present invention is administered as a monotherapy. In one embodiment the antibody is JB5 is administered as monotherapy. In another embodiment the antibody JB5-K74R is administered as monotherapy. In yet another embodiment the antibody JB5-R28K is administered as monotherapy. In still another embodiment the antibody JB5-R28K-K74R is administered as monotherapy.

In some embodiments of the methods according to the present invention, the antibody is administered in combination with another therapeutic agent.

In some embodiments, the antibody of the present invention is administered in combination with a compound that blocks the interaction between CD28 and CD86 or between CD28 and CD80.

In some embodiments the compound that blocks the interaction between CD28 and CD86 or between CD28 and CD80 is a CTLA4-Ig fusion protein. In one embodiment the compound that blocks the interaction between CD28 and CD86 or between CD28 and CD80 is abatacept or belatacept or galiximab.

Pharmaceutical Compositions and Methods of Administration

To treat any of the foregoing disorders, pharmaceutical compositions for use in accordance with the methods of the present disclosure may be formulated in a conventional manner using one or more physiologically acceptable carriers. Pharmaceutically acceptable carriers are determined in part by the particular composition being administered, as well as by the particular method used to administer the composition. Accordingly, there are a wide variety of suitable formulations of the compounds useful in the methods of the present disclosure (see, e.g., Remington: The Science and Practice of Pharmacy, 20th ed., Gennaro et al. Eds., Lippincott Williams and Wilkins, 2000).

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

According to the present disclosure the compounds can be administered by any suitable means, which can vary, depending on the type of disorder being treated and on the nature of the compound itself. For example, for the antibodies of the present invention, administration routes preferably include parenteral, e.g., intramuscular, intravenous, intraarterial, intraperitoneal, or subcutaneous. Preferably, the parenteral dosing is given by injection, most preferably intravenous, intramuscular or subcutaneous injection. The amount to be administered will depend on a variety of factors such as the clinical symptoms, weight of the individual, and whether other drugs are administered. It should be appreciated that determination of proper dosage forms, dosage amounts, and routes of administration is within the level of ordinary skill in the pharmaceutical and medical arts.

EXAMPLES

The following examples illustrate the methods used to make and test the antibodies of the invention. Suitable modifications and adaptations of the described conditions and parameters normally encountered in the art of molecular biology and immunology will be apparent to one of skill in the art.

Example 1: Antibody Production

In order to produce the antibodies of the invention, nucleic acid sequences encoding the heavy chain and the light chain of the desired antibody were designed to be suitable for expression in mammalian cells such as Chinese Hamster Ovary (CHO) cells. The nucleic acids were then artificially synthesized and ligated into the antibody expression vector BPJPuro using standard molecular biology techniques. BPJPuro is a dual gene mammalian expression vector optimized for selectable and stable expression of immunoglobulins in Chinese Hamster Ovary (CHO) cells. The vector is then transfected into CHO cells and stable transfectants selected.

Production of JB5 Antibodies

A nucleic acid (SEQ ID NO:10) encoding a heavy chain having the amino acid sequence of SEQ ID NO:9, and a nucleic acid (SEQ ID NO:8) encoding a light chain having the amino acid sequence of SEQ ID NO:7, were synthesized and ligated into the antibody expression vector BPJPuro.

The resulting expression vector encoding the heavy and light chains was transfected into the CHO line (CHO SA, Cellectis SA, Paris, France) using liposome mediated transfection. Stable transfectants were isolated by puromycin selection and subcloned to provide clonal cell lines. Candidate cell lines were adapted to serum free suspension culture and screened for IgG production and robust growth. One of the cell lines was selected and named JB5, the cell line was cultured in a pilot scale bioreactor and the antibody JB5 was purified from conditioned medium by sequential concentration, Protein A/G affinity chromatography, and size exclusion chromatography.

Example 2: CD40L Binding Assay

A three part sandwich ELISA assay was used to determine binding kinetics of the JB5 antibody relative to the parental antibody hu5c8. All washes were performed using 3 washes of 250 µl of PBS. A 96-well polystyrene plate was coated with 100 µl/well of JB5 or hu5c8 antibody (2 µg/ml) for 16 hours at 4° C. The plate was washed and then blocked with 2% bovine serum albumin/PBS for 1 hour at room temperature. The plate was washed and recombinant human CD40L protein (Santa Cruz Biotechnology, Santa Cruz, Calif., USA) was added to the plate titrated out by 2-fold dilution starting at 2000 ng/ml. After binding and washing, the bound CD40L protein was detected using 100 µl a biotinylated goat anti-human CD40L polyclonal antibody (200 ng/ml) and 100 µl a streptavidin-horseradish peroxidase conjugate at 100 ng/ml. Colorimetric detection was performed with the chromagen TMB (3,3',5,5'-tetramethylbenzidine) and spectrophotometric analysis of absorption at 450 nm. The resulting binding curves (FIG. 3) show that JB5 (circle) has highly similar CD40L binding relative to the parental antibody hu5c8 (square). The control protein CTLA4-IgG1 (triangle), having the same Fc domain as JB5 showed no significant binding. The calculated EC50 for hu5c8 and JB5 is 114 and 137 nM, respectively. JB5-R28K and JB5-K74R showed binding similar to that of JB5.

Figure 4:
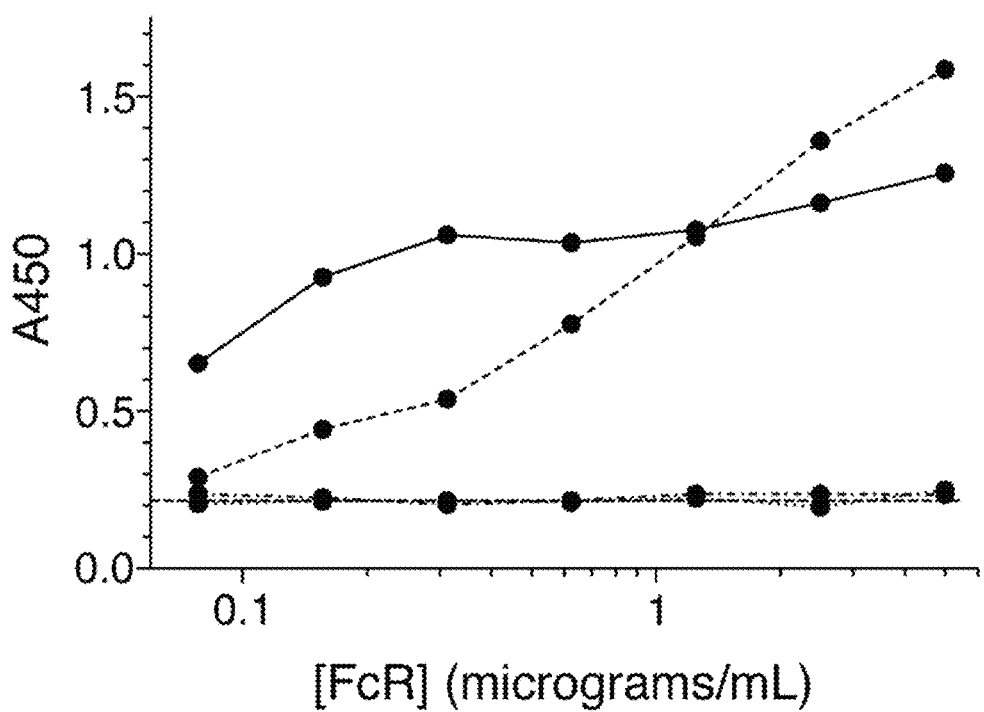
FIG. 4 is a graph showing the binding of hu5c8 antibody to FCGR1A (circle, solid line) (SEQ ID NO:22), FCGR2A (circle, dotted line) (SEQ ID NO:23), FCR3A (SEQ ID NO:24) and FCR3B (SEQ ID NO:25) isoforms of the human Fc gamma receptor protein.

Example 3: Fc Gamma Receptor Binding Assays hu5c8/Human Fc Gamma Receptor Binding Assay A solid phase ELISA binding assay was performed to determine the level of binding of four human Fc gamma receptor isoforms to the parental hu5c8 antibody. 100 µl/well hu5c8 antibody (2 µg/ml in phosphate buffered saline) was added to the wells of a 96 well polystyrene plate and incubated for 16 hours at 4° C. The plate was blocked and recombinant human Fc gamma receptor (FCGR) proteins (Santa Cruz Biotechnology, Santa Cruz, Calif.) titrated by 2-fold dilution with a starting concentration of 5 µg/ml. Four recombinant FCGR isoforms were tested separately as follows: FCGR1A (CD64) (SEQ ID NO:22), FCGR2A (CD32) (SEQ ID NO:23), FCGR3A (CD16a) (SEQ ID NO:24), FCGR3B (CD16b) (SEQ ID NO:25). After binding and washing, the FCGR was detected using an appropriate FCGR isoform specific murine monoclonal antibody (1000 ng/ml) and a horseradish peroxidase conjugate goat anti-mouse IgG detector antibody. Colorimetric detection was performed with the chromagen TMB (3,3',5,5'-tetramethylbenzidine) and spectrophotometric analysis of absorption at 450 nm. The resulting binding curves (FIG. 4) demonstrate that the parental hu5c8 antibody binds the high affinity FCGR1A (circle, solid line) receptor (SEQ ID NO:22) and the FCGR2A receptor (SEQ ID NO:23) (circle, dotted line) expressed on activated platelets, with high affinity. The hu5c8 antibody showed no binding to the FCGR3A receptor (SEQ ID NO:24) or FCGR3B receptor (SEQ ID NO:25) isoforms.

JB5-Human Fc Gamma Receptor Binding Assay

Figure 5:
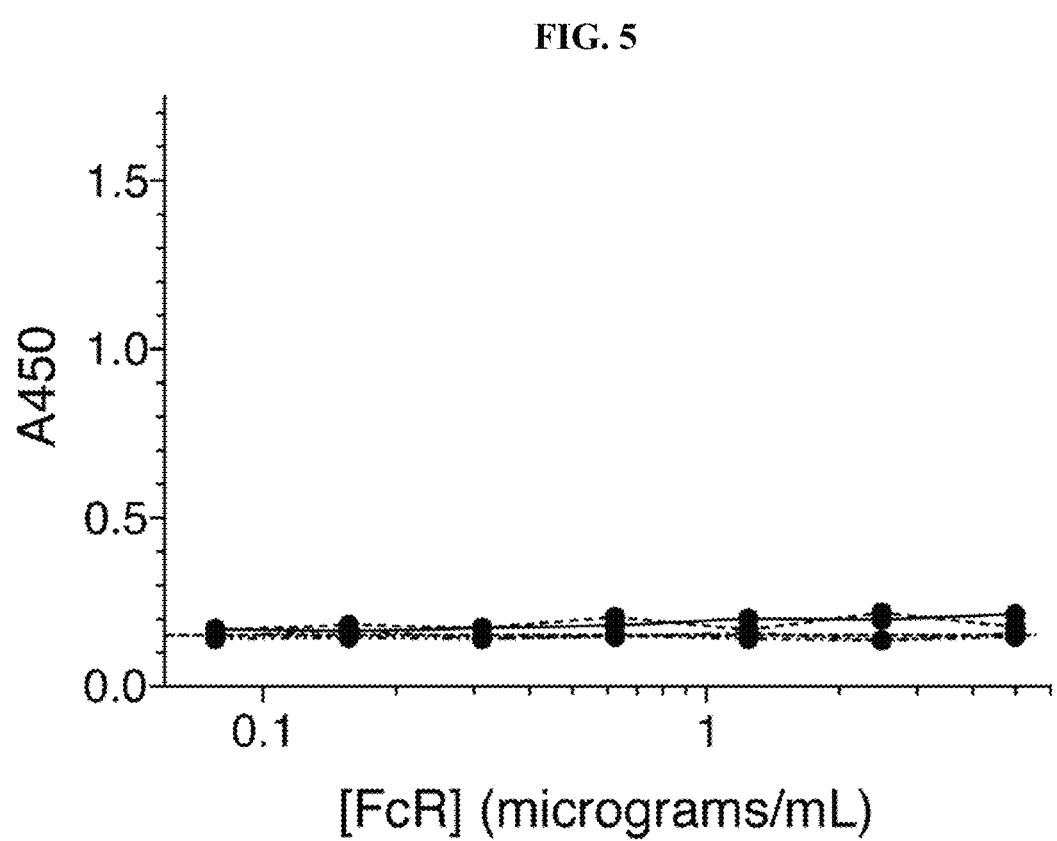
FIG. 5 is a graph showing that JB5 antibody to FCGR1A (SEQ ID NO:22), FCGR2A (SEQ ID NO:23), FCR3A (SEQ ID NO:24), or FCR3B (SEQ ID NO:25) isoforms of the human Fc gamma receptor protein.

A solid phase binding assay was used to test binding of human Fc gamma receptor isoforms to the mutant JB5 antibody. 100 µl/well JB5 (2 µg/ml in phosphate buffered saline) was coated for 16 hours onto a 96 well polystyrene plate. The plate was blocked and recombinant human Fc gamma receptor (FCGR) proteins (Santa Cruz Biotechnology, Santa Cruz, Calif.) titrated onto by 2-fold dilution with a starting concentration of 5 µg/ml. Four recombinant FCGR isoforms were tested separately as follows: FCGR1A (CD64) (SEQ ID NO:22), FCGR2A (CD32) (SEQ ID NO:23), FCGR3A (CD16a) (SEQ ID NO:24), FCGR3B (CD16b) (SEQ ID NO:25). After binding and washing the FCGR was detected using an appropriate FCGR isoform specific murine monoclonal antibody (1000 ng/ml) and a horseradish peroxidase conjugate goat anti-mouse IgG detector antibody. Colorimetric detection was performed with the chromagen TMB (3,3',5,5'-tetramethylbenzidine) and spectrophotometric analysis of absorption at 450 nm. The resulting binding curves (FIG. 5) demonstrate that the JB5 antibody binds neither the high affinity FCGR1A receptor (SEQ ID NO:22) nor the FCGR2A receptor (SEQ ID NO:23), expressed on activated platelets, in this assay. Like the parental hu5c8 antibody, no binding was observed for FCGR3A receptor (SEQ ID NO:24) or FCGR3B receptor (SEQ ID NO:25).

Example 4: Stability of JB5 at 22° C. and at 37° C.

Because JB5 lacks three of the disulfide linkages in wild-type IgG1 antibodies, JB5 was tested using size exclusion chromatography to determine if the antibody was stable, i.e., existed as a tetrameric, fully intact antibody. Hu5c8, which has the three disulfide linkages was used as a control.

Figure 6:
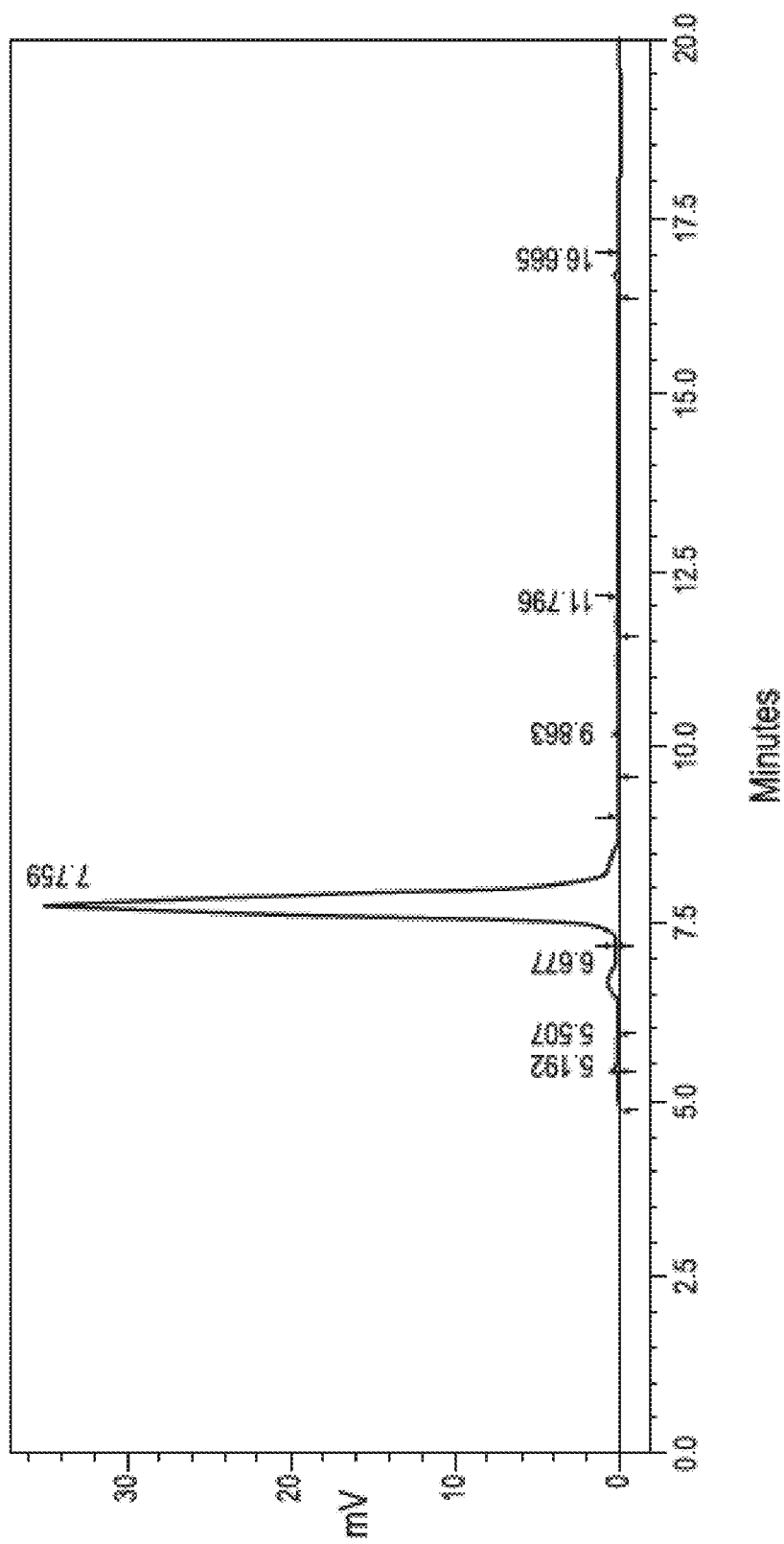
FIG. 6 shows the analytical chromatography elution profile for JB5 antibody run at 30° C. from a size exclusion column.
Figure 7:
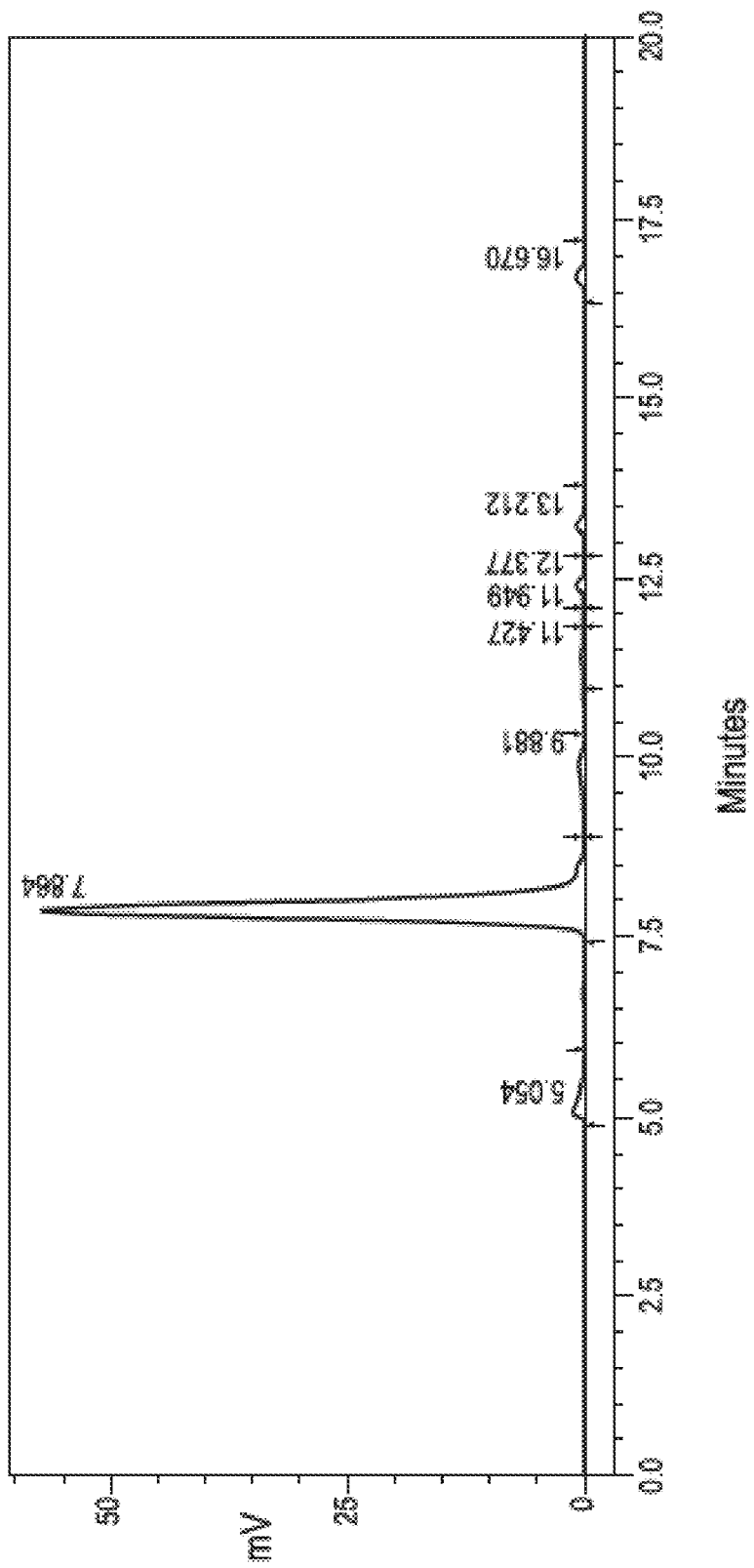
FIG. 7 shows the analytical chromatography elution profile for hu5c8 antibody run at 30° C. from a size exclusion column.

Two experiments were performed, each comparing JB5 with hu5c8. In the first experiment, the antibodies were at room temperature (22° C.) before and during chromatography. To simulate in vivo conditions, in the second experiment the antibodies were incubated in human plasma at 37° C. for 30 minutes prior to chromatography at 30° C. Twenty micrograms of JB5 or hu5c8 in PBS was injected into a TSK® gel G3000SW (7.8 mm×30 cm, 5 µm bead column) equipped with a pre-column filter TSK® gel Guard SW xl, (6.0 mm×4.0 cm, 7 µm bead column) (Tosoh Bioscience, King of Prussia, Pa.). The mobile phase was PBS and the elution rate was 1.0 mL/minute and the absorbance was measured at 280 nm. At both 22° C. and at 30° C. JB5 had an observed molecular weight of 183 kDa (FIG. 6) and hu5c8 (FIG. 7) had a MW of 164 kDa consistent with the antibody being in the tetrameric, divalent form. The observed 19 kDa difference between the hu5c8 antibody and JB5 may be due to increased glycosylation of the Fc domain of JB5.

Example 5: Elimination of Platelet Activation

In order to determine the effect of JB5 on CD40L immune complex mediated platelet activation, the antibody was assayed for its ability to induce the platelet cell surface marker protein PAC-1. Whole blood was drawn from three healthy volunteers into 3.2% Na citrate tubes discarding the first 2 ml. Platelet rich plasma was prepared by centrifugation for 15 minutes at 120 g the platelet count was normalized with phosphate buffered saline to $1 \times 10^5$ cells/ml. Immune complexes of recombinant human CD40L (Santa Cruz Biotechnology, Santa Cruz, Calif., USA) and the test antibodies, hu5c8, JB5, and hu5c8 F(ab')$_2$ were prepared at a CD40L:Antibody molar ratio of 3:1 (0.6944 nmole CD40L:0.2315 nmole antibody) by preincubation at room temperature for 15 minutes. The immune complex mixture was diluted to a final concentration of 5 µg/ml CD40L in the normalized PBS/platelet solution and incubated at 37° C. for 30 minutes. Negative controls were untreated platelets and CD40L alone. The platelet activation positive control was prepared by the addition of ADP to a final concentration of 20 micromolar in the normalized PBS-platelet solution. After 30 minutes of incubation, anti-human PAC-1-FITC conjugated antibody was added to all samples and incubated for 15 minutes. Samples were diluted 1:1 into 2% paraformaldehyde:PBS buffer, fixed on ice for 30 minutes, centrifuged at 100 g, for 5 minutes to pellet the cells. The cells were resuspended in PBS. Fluorescence activated cell sorting (FACS) was performed on a Guava easyCyte flow cytometer (EMD Millipore, Inc., Billerica, Mass., USA). Post-acquisition analysis was performed using FlowJo software (FlowJo, LLC, Ashland, Oreg., USA).

Figure 8:
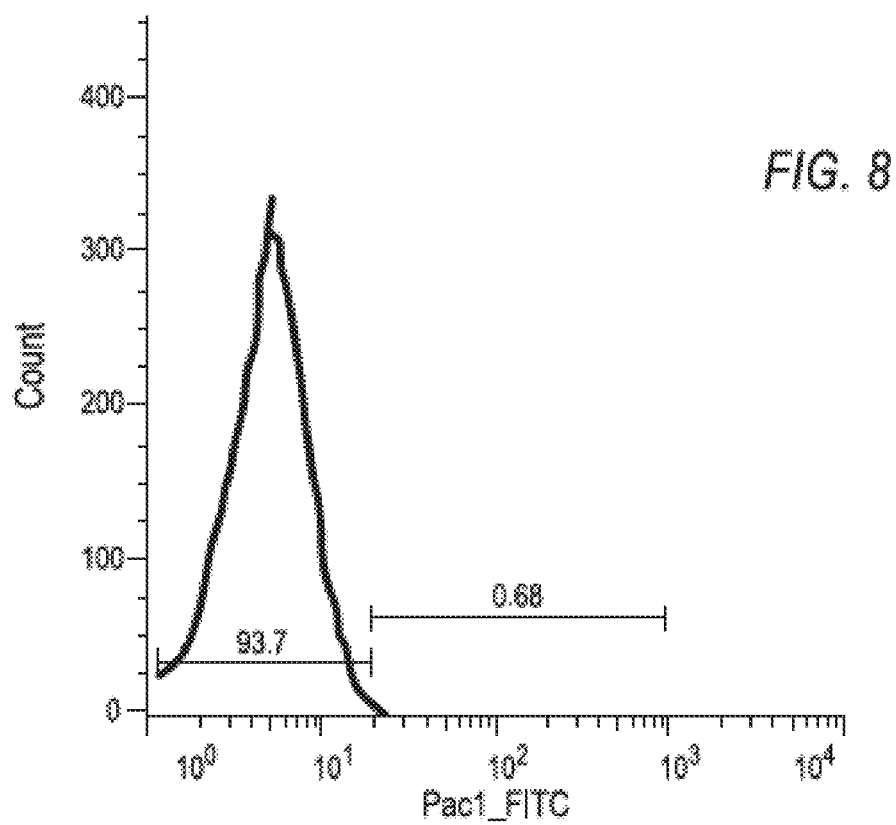
FIG. 8 is a graph showing the binding of the platelet activation marker PAC1 antibody to untreated platelet samples (negative control), as assessed by fluorescence activated cell sorting (FACS).
Figure 9:
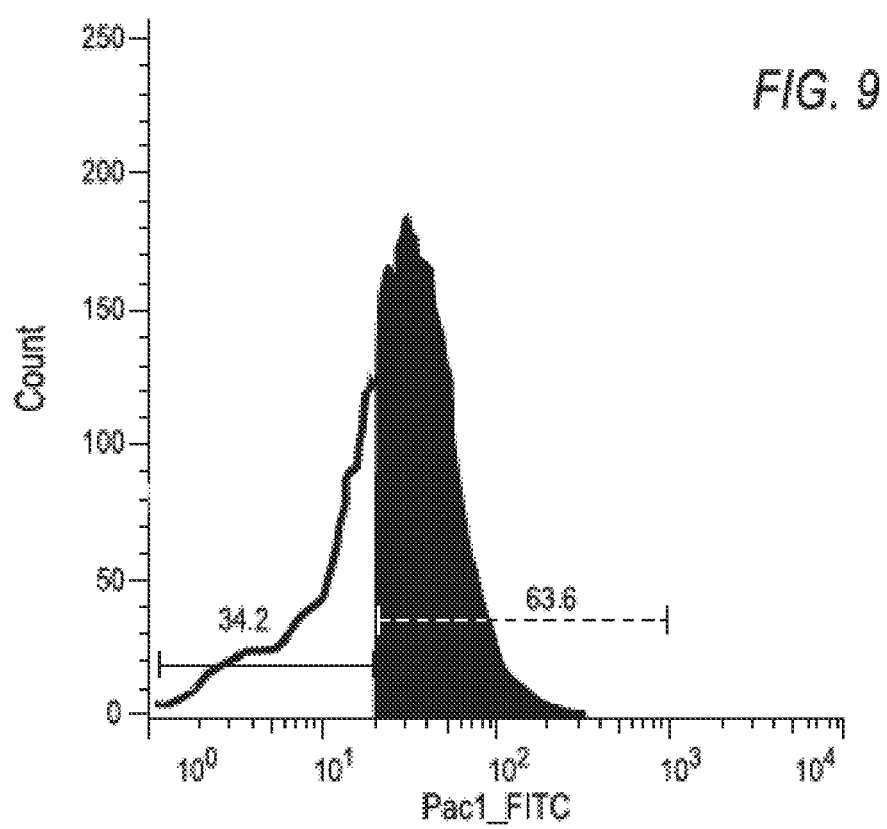
FIG. 9 is a graph showing the binding, as assessed by FACS, of an anti-PAC1 antibody
Figure 10:
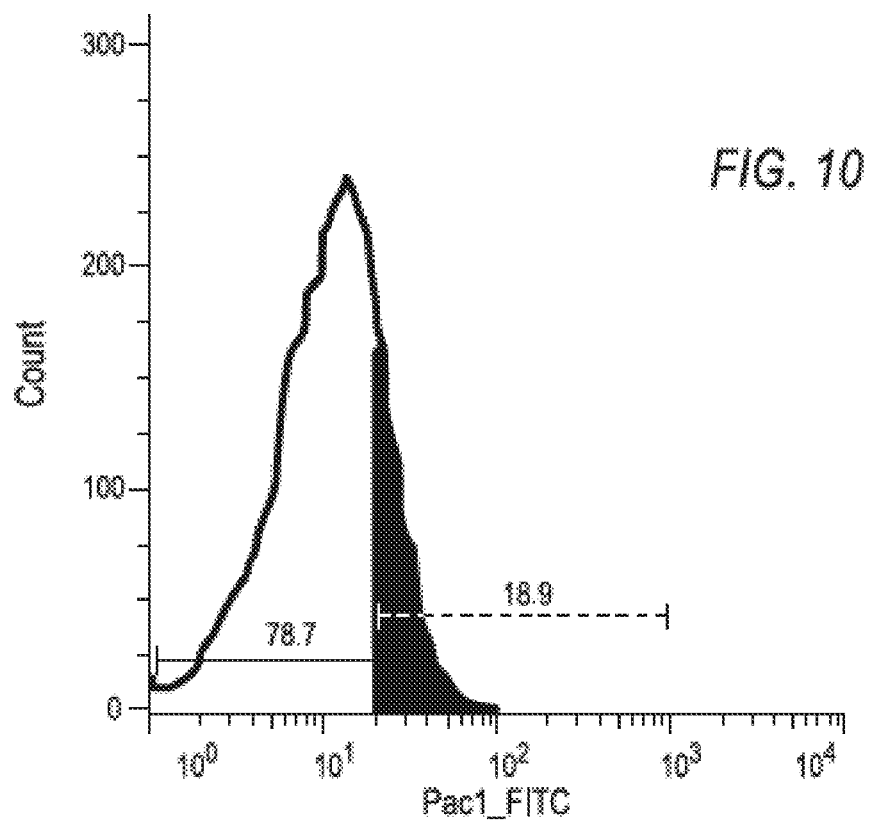
FIG. 10 is a graph showing the binding, as assessed by FACS, of an anti-PAC1 antibody to platelets after the incubation of the platelets with CD40L.
Figure 11:
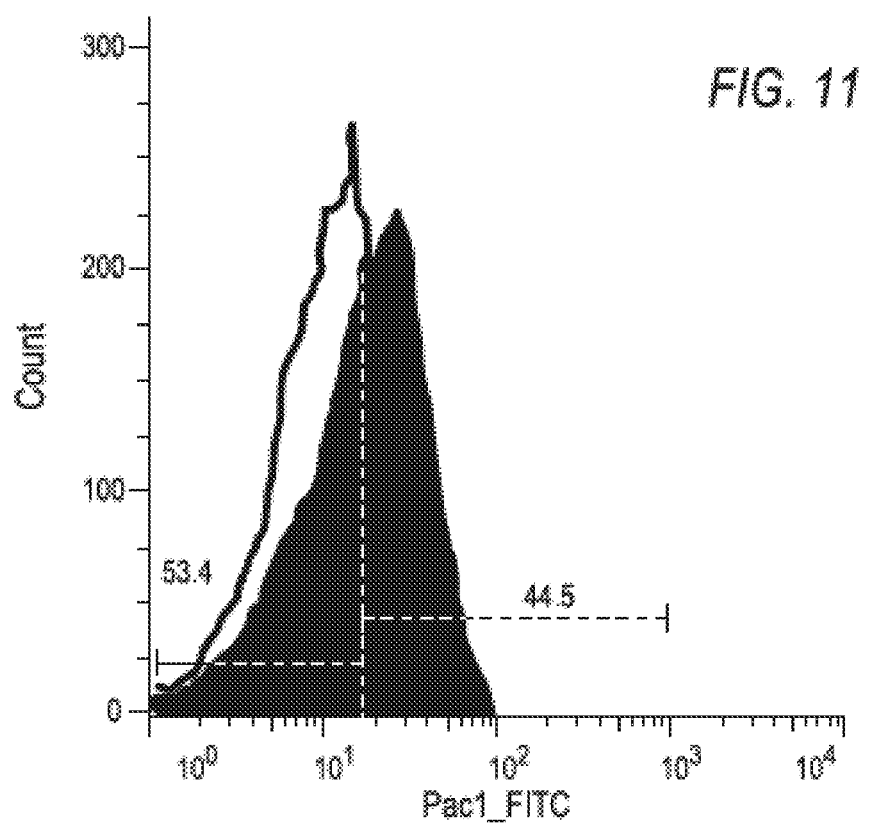
FIG. 11 is a graph showing the binding, as assessed by FACS, of an anti-PAC1 antibody to platelets after incubation of the platelets with an immune complex of CD40L and hu5c8 antibody.
Figure 12:
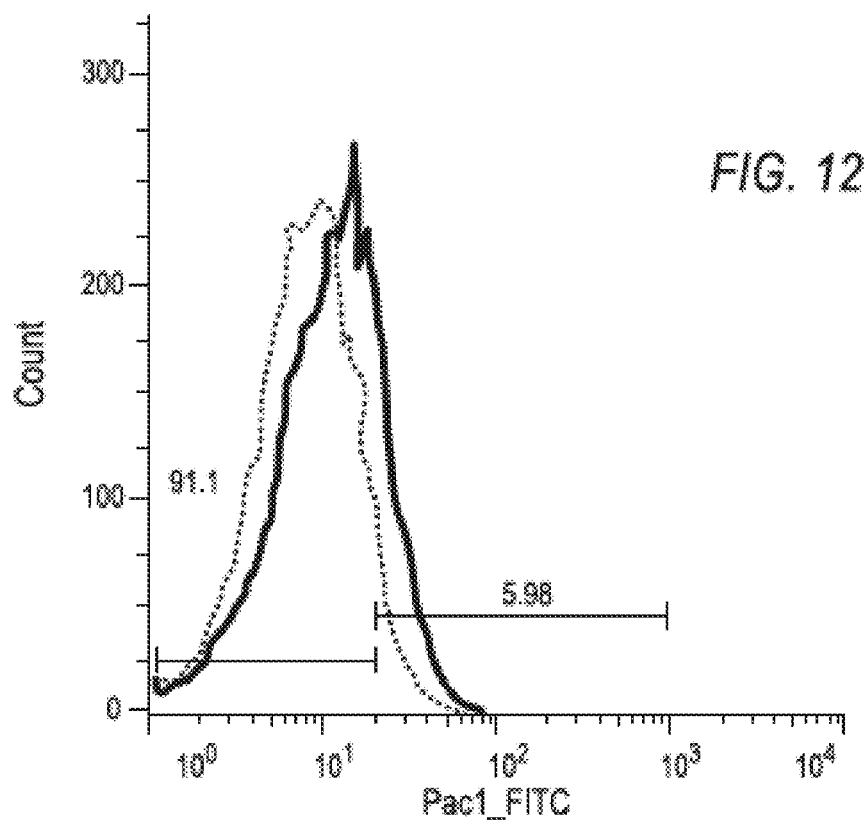
FIG. 12 is a graph showing the binding, as assessed by FACS, of an anti-PAC1 antibody to platelets after incubation of the platelets with an immune complex of CD40L and JB5 antibody.
Figure 13:
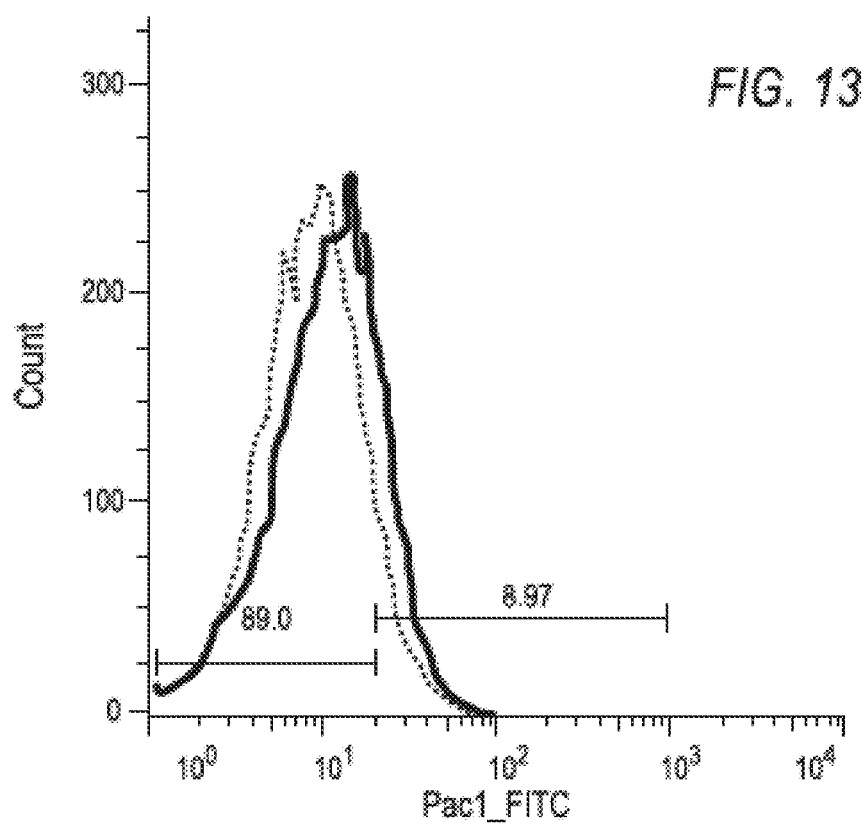
FIG. 13 is a graph showing the binding, as assessed by FACS, of an anti-PAC1 antibody to platelets after incubation of the platelets with an immune complex of CD40L and the hu5c8 F(ab')$_2$.
Figure 14:
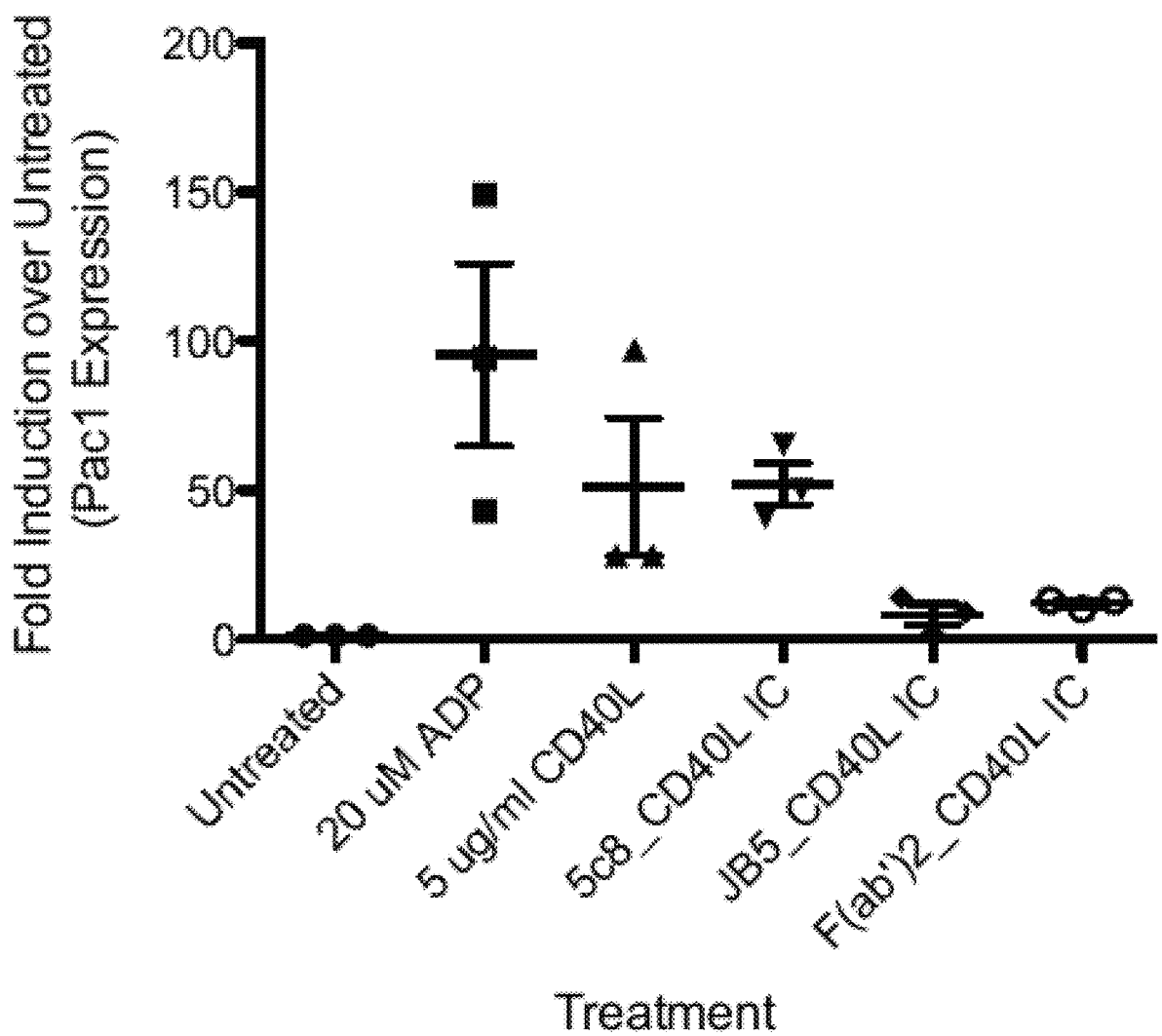
FIG. 14 is a scatter plot graph showing FACS results from three persons' platelets after incubation of the platelets with 20 µM ADP, 5 µg/ml CD40L, the immune complex of CD40L and hu5c8, the immune complex of CD40L and JB5 antibody or the immune complex of CD40L with hu5c8 F(ab')$_2$.

An untreated platelet control sample was used to set negative and positive PAC-1 activation gates (FIG. 8). Platelets activated with 20 micromolar ADP had a significant increase in PAC-1 cell surface expression (FIG. 9). Consistent with published observations, see e.g., Mirabet, M., et al., *Molecular Immunology* 45, 937-944 (2008), CD40L alone was able to activate platelets at a low level (FIG. 10). This activation was significantly increased when CD40L was present with hu5c8 antibody as an immune complex (FIG. 11). In contrast, the engineered antibody JB5 complexed with CD40L demonstrated very low levels of platelet activation (FIG. 12). This reduction in the activation potential of a CD40L:JB5 immune complex is mediated by the loss of FcR interaction because the hu5c8 F(ab')2:CD40L immune complex (FIG. 13) also did not activate platelets relative to the hu5c8-IgG1:CD40L immune complex (FIG. 11). FIG. 14 shows the platelet activation results from three persons' platelets after incubation of the platelets with 20 µM ADP, 5 µg/ml CD40L, the immune complex of CD40L and hu5c8, the immune complex of CD40L and JB5 antibody or the immune complex of CD40L with hu5c8 F(ab')$_2$. The JB5 immune complex showed no significant platelet activation when compared to the immune complex of CD40L with hu5c8 F(ab')$_2$ platelets ($p<0.34$ (Unpaired T test, 2 tailed;

t=1.013, df=4). Further, the JB5 immune complex showed significantly less platelet activation when compared with the hu5c8 immune complex (p<0.005 (Unpaired T test, 2 tailed; t=5.586, df=4).

While a number of embodiments of this disclosure are described, it is apparent that the basic examples may be altered by one skilled in the art to provide other embodiments that use or encompass methods and processes of this invention. The embodiments and examples are for illustrative purposes and are not to be interpreted as limiting the disclosure, but rather, the appended claims define the scope of this invention.

What is claimed is:

1. An isolated antibody that binds to CD40L, wherein the isolated antibody comprises a light chain and a heavy chain, wherein the Fc region consists of the amino acid sequence of SEQ ID NO:4; and
   (i) the light chain variable region consists of the amino acid sequence of SEQ ID NO:1; and the heavy chain variable region consists of the amino acid sequence of SEQ ID NO:2; or
   (ii) the light chain variable region consists of the amino acid sequence of SEQ ID NO:1; and the heavy chain variable region consists of the amino acid sequence of SEQ ID NO:6; or
   (iii) the light chain variable region consists of the amino acid sequence of SEQ ID NO:5; and the heavy chain variable region consists of the amino acid sequence of SEQ ID NO:2; or
   (iv) the light chain variable region consists of the amino acid sequence of SEQ ID NO:5; and the heavy chain variable region consists of the amino acid sequence of SEQ ID NO: 6.

2. The isolated antibody according to claim 1, wherein the Fc region consists of the amino acid sequence of SEQ ID NO:4, and the light chain variable region consists of the amino acid sequence of SEQ ID NO:1, and the heavy chain variable region consists of the amino acid sequence of SEQ ID NO:2.

3. The isolated antibody according to claim 1, wherein the isolated antibody comprises a light chain and a heavy chain, wherein
   (i) the light chain consists of the amino acid sequence of SEQ ID NO:7; and the heavy chain consists of the amino acid sequence of SEQ ID NO:9; or
   (ii) the light chain consists of the amino acid sequence of SEQ ID NO:7; and the heavy chain consists of the amino acid sequence of SEQ ID NO:13; or
   (iii) the light chain consists of the amino acid sequence of SEQ ID NO:11; and the heavy chain consists of the amino acid sequence of SEQ ID NO:9; or
   (iv) the light chain consists of the amino acid sequence of SEQ ID NO:11; and the heavy chain consists of the amino acid sequence of SEQ ID NO:13.

4. A composition comprising an isolated antibody that binds to CD40L, wherein the isolated antibody comprises a light chain and a heavy chain, wherein the Fc region consists of the amino acid sequence of SEQ ID NO:4; and
   (i) the light chain variable region consists of the amino acid sequence of SEQ ID NO:1; and the heavy chain variable region consists of the amino acid sequence of SEQ ID NO:2; or
   (ii) the light chain variable region consists of the amino acid sequence of SEQ ID NO:1; and the heavy chain variable region consists of the amino acid sequence of SEQ ID NO:6; or
   (iii) the light chain variable region consists of the amino acid sequence of SEQ ID NO:5; and the heavy chain variable region consists of the amino acid sequence of SEQ ID NO:2; or
   (iv) the light chain variable region consists of the amino acid sequence of SEQ ID NO:5; and the heavy chain variable region consists of the amino acid sequence of SEQ ID NO: 6.

5. The composition according to claim 4, wherein the Fc region consists of the amino acid sequence of SEQ ID NO:4, and the light chain variable region consists of the amino acid sequence of SEQ ID NO:1, and the heavy chain variable region consists of the amino acid sequence of SEQ ID NO:2.

6. The composition according to claim 4, wherein the isolated antibody comprises a light chain and a heavy chain, wherein
   (i) the light chain consists of the amino acid sequence of SEQ ID NO:7; and the heavy chain consists of the amino acid sequence of SEQ ID NO:9; or
   (ii) the light chain consists of the amino acid sequence of SEQ ID NO:7; and the heavy chain consists of the amino acid sequence of SEQ ID NO:13; or
   (iii) the light chain consists of the amino acid sequence of SEQ ID NO:11; and the heavy chain consists of the amino acid sequence of SEQ ID NO:9; or
   (iv) the light chain consists of the amino acid sequence of SEQ ID NO:11; and the heavy chain consists of the amino acid sequence of SEQ ID NO:13.

7. A pharmaceutical composition comprising an isolated antibody that binds to CD40L, wherein the isolated antibody comprises a light chain and a heavy chain, wherein the Fc region consists of the amino acid sequence of SEQ ID NO:4; and
   (i) the light chain variable region consists of the amino acid sequence of SEQ ID NO:1; and the heavy chain variable region consists of the amino acid sequence of SEQ ID NO:2; or
   (ii) the light chain variable region consists of the amino acid sequence of SEQ ID NO:1; and the heavy chain variable region consists of the amino acid sequence of SEQ ID NO:6; or
   (iii) the light chain variable region consists of the amino acid sequence of SEQ ID NO:5; and the heavy chain variable region consists of the amino acid sequence of SEQ ID NO:2; or
   (iv) the light chain variable region consists of the amino acid sequence of SEQ ID NO:5; and the heavy chain variable region consists of the amino acid sequence of SEQ ID NO: 6, and the pharmaceutical composition further comprises a physiologically acceptable carrier.

8. The pharmaceutical composition according to claim 7, wherein the Fc region consists of the amino acid sequence of SEQ ID NO:4, and the light chain variable region consists of the amino acid sequence of SEQ ID NO:1, and the heavy chain variable region consists of the amino acid sequence of SEQ ID NO:2, and the pharmaceutical composition further comprises a physiologically acceptable carrier.

9. The pharmaceutical composition according to claim 7, wherein the isolated antibody comprises a light chain and a heavy chain, wherein (i) the light chain consists of the amino acid sequence of SEQ ID NO:7; and the heavy chain consists of the amino acid sequence of SEQ ID NO:9; or
(ii) the light chain consists of the amino acid sequence of SEQ ID NO:7; and the heavy chain consists of the amino acid sequence of SEQ ID NO:13; or
(iii) the light chain consists of the amino acid sequence of SEQ ID NO:11; and the heavy chain consists of the amino acid sequence of SEQ ID NO:9; or
(iv) the light chain consists of the amino acid sequence of SEQ ID NO:11; and the heavy chain consists of the amino acid sequence of SEQ ID NO:13.

10. A pharmaceutical composition comprising an isolated antibody that binds to CD40L, wherein the isolated antibody comprises a light chain and a heavy chain, wherein the light chain consists of SEQ ID NO: 7; and the heavy chain consists of the amino acid sequence of SEQ ID NO:9, and the pharmaceutical composition further comprises a physiologically acceptable carrier.

* * * * *